US010576283B2

(12) United States Patent
Flaherty et al.

(10) Patent No.: US 10,576,283 B2
(45) Date of Patent: Mar. 3, 2020

(54) BRAIN STIMULATION SYSTEM INCLUDING MULTIPLE STIMULATION MODES

(71) Applicant: Functional Neuromodulation Inc., Toronto (CA)

(72) Inventors: J. Christopher Flaherty, Auburndale, FL (US); Daniel J. O'Connell, Earlysville, VA (US); Todd Langevin, Edina, MN (US); R. Maxwell Flaherty, Auburndale, FL (US)

(73) Assignee: Functional Neuromodulation, Inc. (CA)

( * ) Notice: Subject to any disclaimer, the term of this patent is extended or adjusted under 35 U.S.C. 154(b) by 0 days.

(21) Appl. No.: 15/431,569

(22) Filed: Feb. 13, 2017

(65) Prior Publication Data

US 2017/0151436 A1 Jun. 1, 2017

Related U.S. Application Data

(63) Continuation of application No. PCT/CA2015/050768, filed on Aug. 13, 2015.
(Continued)

(51) Int. Cl.
*A61N 1/36* (2006.01)
*A61N 5/06* (2006.01)
(Continued)

(52) U.S. Cl.
CPC .......... *A61N 1/36082* (2013.01); *A61B 5/021* (2013.01); *A61B 5/02055* (2013.01);
(Continued)

(58) Field of Classification Search
CPC ............ A61N 1/36064; A61N 1/36082; A61N 1/36146; A61N 1/36132; A61N 2/004; A61N 2/006; A61N 2/02; A61B 5/02055
See application file for complete search history.

(56) References Cited

U.S. PATENT DOCUMENTS 7,808,897 B1 10/2010 Mehta et al.
8,000,795 B2 8/2011 Lozano
(Continued)

FOREIGN PATENT DOCUMENTS

WO WO-2007090054 A2 8/2007
WO WO-2011133583 A1 10/2011
WO WO-2015149170 A1 10/2015

OTHER PUBLICATIONS

"EP15832450.9 Extended Search Report dated Mar. 19, 2018".
International search report and written opinion dated Nov. 2, 2015 for PCT/CA2015/050768.

*Primary Examiner* — Carrie R Dorna
(74) *Attorney, Agent, or Firm* — Wilson Sonsini Goodrich & Rosati

(57) ABSTRACT

A system for treating a patient comprises a stimulator for stimulating brain tissue, a controller for setting stimulation parameters and a diagnostic tool for measuring patient parameters and producing diagnostic data. The stimulation parameters comprise test stimulation parameters and treatment stimulation parameters. The stimulator delivers test stimulation energy to the brain tissue based on at least one test stimulation parameter and delivers treatment stimulation energy to the brain tissue based on at least one treatment stimulation parameter. One or more treatment stimulator parameters are determined based on the diagnostic data produced by the diagnostic tool The system is constructed and arranged to treat a neurological disease or a neurological disorder. Methods of treating a neurological disease or neurological disorder are also provided.

26 Claims, 3 Drawing Sheets

Related U.S. Application Data

(60) Provisional application No. 62/037,524, filed on Aug. 14, 2014.

(51) Int. Cl.

| | | |
|---|---|---|
| *A61N 1/05* | (2006.01) | |
| *A61B 6/03* | (2006.01) | |
| *A61B 6/00* | (2006.01) | |
| *A61B 5/0205* | (2006.01) | |
| *A61B 5/0402* | (2006.01) | |
| *A61B 5/0476* | (2006.01) | |
| *A61B 5/053* | (2006.01) | |
| *A61B 5/11* | (2006.01) | |
| *A61B 5/145* | (2006.01) | |
| *A61B 5/00* | (2006.01) | |
| *A61B 5/021* | (2006.01) | |
| *A61B 5/055* | (2006.01) | |
| *A61N 2/00* | (2006.01) | |
| *A61N 7/00* | (2006.01) | |

(52) U.S. Cl.
CPC .......... *A61B 5/0402* (2013.01); *A61B 5/0476* (2013.01); *A61B 5/055* (2013.01); *A61B 5/0531* (2013.01); *A61B 5/1118* (2013.01); *A61B 5/14532* (2013.01); *A61B 5/14539* (2013.01); *A61B 5/14542* (2013.01); *A61B 5/14546* (2013.01); *A61B 5/4064* (2013.01); *A61B 5/4076* (2013.01); *A61B 5/4806* (2013.01); *A61B 5/4836* (2013.01); *A61B 6/032* (2013.01); *A61B 6/037* (2013.01); *A61B 6/487* (2013.01); *A61N 1/0531* (2013.01); *A61N 1/0534* (2013.01); *A61N 1/36064* (2013.01); *A61N 1/36067* (2013.01); *A61N 1/36096* (2013.01); *A61N 1/36139* (2013.01); *A61N 1/36146* (2013.01); *A61N 2/002* (2013.01); *A61N 2/006* (2013.01); *A61N 5/0622* (2013.01); *A61N 7/00* (2013.01); *A61N 1/36121* (2013.01); *A61N 2007/0026* (2013.01)

(56) References Cited

U.S. PATENT DOCUMENTS

| | | |
|---|---|---|
| 8,078,275 B2 | 12/2011 | Lozano |
| 8,612,006 B2 | 12/2013 | Lozano et al. |
| 2007/0179558 A1 | 8/2007 | Gliner et al. |
| 2011/0160796 A1 | 6/2011 | Lane et al. |
| 2011/0224571 A1 | 9/2011 | Pascual-Leone et al. |
| 2013/0131754 A1 | 5/2013 | Sarvazyan |
| 2013/0289385 A1 | 10/2013 | Lozano et al. |

BRAIN STIMULATION SYSTEM INCLUDING MULTIPLE STIMULATION MODES

CROSS-REFERENCE TO RELATED APPLICATIONS

This application is a continuation of International Patent Application No. PCT/CA2015/050768 filed Aug. 13, 2015, which claims priority under 35 USC 119(3) to U.S. Provisional Patent Application Ser. No. 62/037,524, titled "Brain Stimulation System including Multiple Stimulation Modes", filed Aug. 14, 2014, the content of which is incorporated herein by reference in its entirety.

This application is related to U.S. patent Ser. No. 11/303,293, entitled "Cognitive Function within a Human Brain", filed Dec. 16, 2005; U.S. patent Ser. No. 11/303,292, titled "Inducing Neurogenesis within a Human Brain", filed Dec. 16, 2005; U.S. patent Ser. No. 11/303,619, titled "Regulation of Neurotrophins", filed Dec. 16, 2005; U.S. patent application Ser. No. 11/365,977, titled "Method of Treating Cognitive Disorders Using Neuromodulation", filed Mar. 1, 2006; U.S. patent application Ser. No. 13/655,652, titled "Deep Brain Stimulation of Memory Circuits in Alzheimer's Disease", filed Oct. 19, 2012; International PCT Patent Application Serial Number PCT/US2014/060923, titled "Brain Stimulation System including Diagnostic Tool", filed Oct. 16, 2014; and International PCT Patent Application Serial Number PCT/CA2015/050249, titled "Systems and Methods for Determining a Trajectory for a Brain Stimulation Lead", filed Mar. 31, 2014; the contents of which are each incorporated herein by reference in their entirety.

FIELD OF INVENTION

The present invention relates generally to methods and systems for treating a neurological disease or disorder, such as Alzheimer's Disease or other cognitive disorder. In particular, a system includes a stimulation device that operates in two or more stimulation modes.

BACKGROUND OF THE INVENTION

Brain stimulation has been performed to treat numerous patient diseases and disorders, such as neurological and psychiatric conditions. Both invasive and non-invasive technologies have been developed. One non-invasive system includes a transcranial magnetic stimulation device that directs a magnetic field from outside the patient's head to induce electric currents in the patient's brain. Deep brain stimulation (DBS) can be accomplished using surgically implanted electrodes that deliver electrical stimulation to precisely targeted areas in the brain. More than 100,000 patients have been implanted with deep brain electrodes, and its predominant application has been in the treatment of movement disorders, most commonly Parkinson's disease.

There is a need for enhanced DBS and other brain stimulation systems, devices and methods that result in increased safety and improved efficacy in the treatment of patients.

SUMMARY OF THE INVENTION

According to an aspect of the invention, a system for treating a patient comprises a stimulator for stimulating brain tissue and a controller for setting stimulation parameters of the stimulator, and the stimulator can be configured to operate in a first mode with a first set of stimulation parameters and a second mode with a second set of stimulation parameters different from the first set of stimulation parameters, and the system can be configured to treat at least one of a cognitive disease or a cognitive disorder.

In some embodiments, the cognitive disease or disorder comprises a disease or disorder selected from the group consisting of: Alzheimer's Disease (AD) such as Mild or Moderate Alzheimer's Disease; probable Alzheimer's Disease; a genetic form of Alzheimer's Disease; Mild Cognitive Impairment (MCI); hippocampal damage such as hippocampal damage and/or hippocampal atrophy due to Alzheimer's disease, anoxia, epilepsy, depression; post-traumatic stress disorder (PTSD); traumatic brain injury (TBI); neuronal loss; neuronal damage; chemotherapy induced memory impairment; epilepsy; a seizure disorder; dementia; amnesia; a memory disorder such a spatial memory disorder; traumatic brain injury; cognitive impairment associated with Schizophrenia; Parkinson's Disease related cognitive impairment or dementia; a neurological condition; a psychiatric condition; and combinations thereof.

In some embodiments, the system is configured to treat negative symptoms of a disease or disorder selected from the group consisting of: schizophrenia; depression; post-traumatic stress disorder (PTSD); traumatic brain injury (TBI); other conditions of reversible impaired memory or cognition; Parkinson's Disease; and combinations thereof.

In some embodiments, the system utilizes less power when the stimulator is in the first mode than when the stimulator is in the second mode.

In some embodiments, the system is configured to provide an enhanced memory recall effect when the stimulator is in the second mode.

In some embodiments, the stimulator is configured to deliver stimulation energy, and the stimulation energy delivered in the first mode is different than the stimulation energy delivered in the second mode. The stimulation energy difference can comprise a difference in the type of stimulation energy delivered. The stimulation energy delivered in the first mode can comprise energy selected from the group consisting of: electrical energy; magnetic field energy; light energy; energy configured to optogenetically induce neurons; sound energy; chemical energy; and combinations thereof. The stimulation energy difference can comprise a difference in the magnitude of energy delivered. The difference in the magnitude of energy delivered can comprise a difference in energy delivered over time. The difference in the magnitude of energy delivered can comprise a difference in average energy delivered within a time period. The difference in the magnitude of energy delivered can comprise a difference in peak energy delivered within a time period. The difference in the magnitude of energy delivered can comprise a difference in at least 5% in magnitude of energy delivered. The difference in the magnitude of energy delivered can comprise a difference in at least 10% in magnitude of energy delivered. The difference in the magnitude of energy delivered can comprise a difference in at least 25% in magnitude of energy delivered. The difference in the magnitude of energy delivered can comprise a difference in at least 50% in magnitude of energy delivered. The difference in the magnitude of energy delivered can comprise a difference in at least 100% in magnitude of energy delivered. The stimulation difference can comprise a difference in an energy delivery parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; and combinations thereof. The stimulation energy can comprise electrical energy, and the stimulation difference comprises a difference in an electrical energy deliver parameter selected from the group consisting of: voltage level; average voltage level; peak voltage level; current level; average current level; peak current level; power level; average power level; peak power level; frequency; phase; duty cycle; pulse width; modulation; and combinations thereof. The stimulation energy can comprise electrical energy, and at least one of the first set of stimulation parameters or the second set of stimulation parameters comprises a duty cycle of approximately 1%. The at least one of the first set of stimulation parameters or the second set of stimulation parameters can comprise an on time of approximately 90 μsecs. The stimulation energy can comprise electrical energy, and at least one of the first set of stimulation parameters or the second set of stimulation parameters comprises a voltage of at least 3.0V. The stimulation energy can comprise electrical energy, and at least one of the first set of stimulation parameters or the second set of stimulation parameters comprises a frequency of between 2 Hz and 1000 Hz. The energy delivered between 2 Hz and 1000 Hz can be delivered intermittently. The energy delivered between 2 Hz and 1000 Hz can be delivered at approximately 5 Hz. The energy delivered between 2 Hz and 1000 Hz can be delivered at approximately 100 Hz. The energy delivered between 2 Hz and 1000 Hz can be delivered at approximately 130 Hz. The energy delivered between 2 Hz and 1000 Hz can be delivered as Theta Burst stimulation energy. The Theta Burst stimulation energy can comprise energy delivered at approximately 200 Hz in multiple trains of pulses. The multiple trains can comprise trains of approximately 50 msec in duration. The trains can be delivered at a rate of approximately 5 trains/second. The stimulation energy can comprise light energy, and the stimulation difference comprises a difference in a light energy deliver parameter selected from the group consisting of: intensity; average intensity; peak intensity; power level; average power level; peak power level; frequency; phase; pulse width; modulation; and combinations thereof. The stimulation energy can comprise sound energy, and the stimulation difference comprises a difference in a sound energy deliver parameter selected from the group consisting of: intensity; average intensity; peak intensity; power level; average power level; peak power level; frequency; phase; pulse width; modulation; and combinations thereof. The stimulation energy can comprise energy delivered by an agent, and the stimulation difference comprises a difference in an agent delivery parameter selected from the group consisting of: agent delivery rate; flow rate; concentration of agent being delivered; and combinations thereof. The stimulator can comprise a first stimulation element and a second stimulation element, and the first stimulation element delivers energy in the first mode and the second stimulation element delivers energy in the second mode. Both the first stimulation element and the second stimulation element can deliver energy in the second mode. In some embodiments, the first stimulation element does not deliver energy in the second mode. The at least one of the first stimulation element or the second stimulation element can comprise an electrode. The stimulator can further comprise a stimulation lead, and the first stimulation element and the second stimulation element are positioned on the stimulation lead.

In some embodiments, the system further comprises a battery, and the energy drain from the battery is greater when the stimulator is operator in the second mode than in the first mode. The first set of stimulation parameters can comprise a parameter with a lower value than a corresponding parameter in the second set of stimulation parameters, and the first stimulation parameter comprises a parameter selected from the group consisting of: average energy delivered; cumulative energy delivered; peak energy delivered; duty cycle for energy delivery; voltage of energy delivered; current of energy delivered; intensity of energy delivered; and combinations thereof.

In some embodiments, the tissue stimulated in the first mode comprises a first volume of brain tissue, and the tissue stimulated in the second mode comprises a second volume of brain tissue, and at least a portion of the second volume of tissue comprises tissue not included in the first volume of tissue. The second volume of tissue can comprise a larger volume than the first volume of tissue. The second volume of tissue can comprise the first volume of tissue and tissue not included in the first volume of tissue.

In some embodiments, the stimulator is configured to stimulate with the first stimulation parameters for multiple discrete first time periods and to stimulate with the second stimulation parameters for multiple discrete second time periods. The stimulator can be configured to repeatedly alternate between stimulating with the first set of stimulation parameters and the second set of stimulation parameters. The multiple discrete first time periods can each comprise similar durations of time. The multiple discrete second time periods can each comprise similar durations of time. The stimulator can be configured to initiate each stimulation using the second set of stimulation parameters based on the occurrence of an event. The event can comprise a patient event. The patient event can comprise an event selected from the group consisting of: inability to recall a memory event; inability to access a memory engram; frustration; anger; disorientation; and combinations thereof. The system can further comprise a sensor configured to produce a signal and an algorithm, the event comprises a patient event detected by the algorithm based on the sensor signal. The sensor can comprise a sensor selected from the group consisting of: electrode; neuronal activity sensor; EEG sensor; polysomnography (PSG) sensor; sleep sensor; sleep state sensor; local field potential sensor; neurochemical sensor; EKG sensor; pH sensor; pressure sensor; blood pressure sensor; respiration sensor; acoustic sensor; optical sensor; blood gas sensor; blood glucose sensor; glucose sensor; insulin sensor; blood oxygen sensor; eye movement sensor; blink rate sensor; magnetic sensor; strain gauge; temperature sensor; and combinations thereof. The system can further comprise a switch, and the event comprises activation of the switch by an operator. The operator can comprise the patient. The at least one of: the multiple discrete first time periods or the multiple discrete second time periods, can each comprise different durations of time. The multiple discrete first time periods can each comprise different durations of time and the multiple discrete second time periods can each comprise different durations of time. Each discrete first time period can comprise at least 5 minutes, and each discrete second time period can comprise at least 30 seconds. Each discrete first time period can comprise at least 1 hour, and each discrete second time period can comprise at least 30 seconds. Each discrete first time period can comprise at least 24 hours, and each discrete second time period can comprise at least 30 seconds. Each discrete first time period can comprise at least 5 minutes, and each discrete second time period can comprise at least 5 minutes. Each discrete first time period can comprise at least 1 hour, and each discrete second time period can comprise at least 1 hour. Each discrete first time period can comprise at least 24 hours, and each discrete second time period can comprise at least 24 hours. The stimulator can be configured to deliver more power in each discrete second time period than the power delivered in each discrete first time period. The stimulator can be configured to deliver no energy in at least one first time period.

In some embodiments, the stimulator transitions from the first mode to the second mode when the stimulator has operated in the first mode for a pre-determined time period. The stimulator can transition from the second mode to the first mode when the stimulator has operated in the second mode for a pre-determined time period.

In some embodiments, the system further comprises an electronic clock, and the stimulator transitions between the first mode and the second mode based on the time of day determined by the electronic clock. The stimulator can operate in the second mode for at least a portion of nighttime. The stimulator can deliver less power in the second mode than the power delivered in the first mode. The stimulator can deliver more power in the second mode than the power delivered in the first mode.

In some embodiments, the stimulator can be configured to transition between the first mode and the second mode based on a patient parameter. The stimulator can be configured to transition between the first mode and the second mode based on a change in the patient parameter. The system can further comprise a threshold, and the stimulator can be configured to transition between the first mode and the second mode when the patient parameter exceeds the threshold. The system can further comprise a sensor configured to produce a signal related to the patient parameter. The system can further comprise an algorithm configured to assess the sensor signal and determine if the patient parameter exceeds the threshold. The patient parameter can comprise a circadian rhythm parameter. The patient parameter can comprise a patient awakeness parameter, and the stimulator can transition from the first mode to the second mode as the patient falls asleep or transitions from one sleep state to another (e.g. as determined by one or more sensors). The stimulator can be configured to deliver less energy to brain tissue when in the second mode than the energy delivered to brain tissue when in the first mode. The stimulator can be configured to deliver more energy to brain tissue when in the second mode than the energy delivered to brain tissue when in the first mode. The system can further comprise a sensor configured to produce a signal related to patient awakeness and an algorithm configured to assess patient awakeness based on the sensor signal. The patient parameter can comprise a patient activity level parameter. The system can further comprise a threshold, and the stimulator can be configured to transition from the first mode to the second mode when the patient activity level exceeds the threshold. The system can further comprise a sensor configured to produce a signal related to the patient activity level parameter and an algorithm configured to assess the sensor signal and to determine if the patient activity level parameter has exceeded the threshold. The stimulator can be configured to deliver less energy to brain tissue when in the second mode than the energy delivered to brain tissue when in the first mode. The stimulator can be configured to deliver more energy to brain tissue when in the second mode than the energy delivered to brain tissue when in the first mode. The patient parameter can comprise a patient activity parameter, and the stimulator can be configured to transition from the first mode to the second mode when a particular patient activity is detected. The patient activity parameter can be related to a patient activity selected from the group consisting of: reading; writing; talking; participating in a conversation; and combinations thereof. The system can further comprise a sensor configured to produce a signal related to the patient activity parameter and an algorithm configured to assess the sensor signal and to determine if the patient activity parameter has exceeded the threshold. The patient parameter can be related to a patient physiologic parameter selected form the group consisting of: blood pressure; heart rate; eye movement; blink rate; respiration; a glucose level; an insulin level; a theta rhythm state; a sleep state; one or more brain signals; one or more heart signals; and combinations thereof. The system can further comprise a sensor configured to produce a signal related to the patient physiologic parameter and an algorithm configured to assess the sensor signal and to determine if the patient physiologic parameter has exceeded the threshold. The patient parameter can be related to the patient's ability to recall a memory event. The stimulator can be configured to deliver no energy to brain tissue when in the first mode. The stimulator can be configured to deliver more power to brain tissue when in the second mode than the power delivered to brain tissue when in the first mode. The system can further comprise an algorithm configured to detect the patient's inability to recall the memory event. The algorithm can be biased toward false positives. The system can further comprise a sensor configured to produce a signal related to the patient's ability to recall a memory event. The system can further comprise an algorithm configured to assess the sensor signal and to determine if the patient's ability to recall a memory event exceeds a threshold. The algorithm can be biased toward false positives.

In some embodiments, the stimulator can be configured to transition between the first mode and the second mode based on an operator action. The operator comprises an operator selected from the group consisting of: the patient; a clinician; a healthcare provider; a family member; and combinations thereof. The system can further comprise a switch, and the system can be configured to transition between the first mode and the second mode upon operation activation of the switch. The switch can comprise a patient activatable switch. The switch can be configured to be activated by the patient in an attempt to recall a memory event. The switch can be configured to be activated by the patient while experiencing an inability to recall a memory event.

In some embodiments, the system further comprises a sensor configured to produce a signal. The stimulator can be configured to transition between the first mode and the second mode based on the sensor signal. The system can further comprise an algorithm configured to assess the sensor signal and to cause the stimulator to transition between the first mode and the second mode based on the assessment. The algorithm can comprise a bias. The algorithm can be biased toward false positives. The sensor signal can be related to the patient's inability to recall a memory event and/or the sensor signal can be related to patient's sleep status. The algorithm can be biased toward false negatives. The sensor signal can be related to the patient's sleep status. The stimulator can be configured to deliver more energy to brain tissue when in the second mode than the energy delivered to brain tissue in the first mode. The sensor can comprise a sensor selected from the group consisting of: electrode; neuronal activity sensor; EEG sensor; polysomnography (PSG) sensor; sleep sensor; sleep state sensor; local field potential sensor; neurochemical sensor; EKG sensor; pH sensor; pressure sensor; blood pressure sensor; respiration sensor; acoustic sensor; optical sensor; blood gas sensor; blood glucose sensor; glucose sensor; insulin sensor; blood oxygen sensor; eye movement sensor; blink rate sensor; magnetic sensor; strain gauge; temperature sensor; and combinations thereof.

In some embodiments, the stimulator is configured to transition from the first mode to the second mode at a trigger event, and the stimulator is configured to remain in the second mode for a pre-determined time period. The pre-determined time period can comprise a time period less than 4 hours. The pre-determined time period can comprise a time period less than 1 hour. The trigger event can comprise an event selected from the group consisting of: operator activation of a switch; a patient event; a patient physiologic event; a patient event detected by a sensor; and combinations thereof. The stimulator can be configured to deliver more power to brain tissue when in the second mode than the energy delivered to brain tissue when in the first mode. The stimulator can be configured to deliver no energy to brain tissue when in the first mode.

In some embodiments, the stimulator can be further configured to operate in a third mode with a third set of stimulation parameters different than the first set of stimulation parameters and the second set of stimulation parameters.

In some embodiments, the controller comprises a switch configured such that activation of the switch by an operator transitions the stimulator from operating in the first mode to operating in the second mode. The switch can be further configured such that activation of the switch by an operator transitions the stimulator from operating in the second mode to operating in the first mode. The system can be configured to prevent the stimulator from transitioning from the second mode to the first mode by activation of the switch. The system can be configured to automatically transition the stimulator from operating in the second mode to operation in the first mode. The system can be configured to automatically perform the transition after the stimulator is operating in the second mode for a pre-determined time duration. The stimulator can be configured to deliver more energy to brain tissue when in the second mode than the energy delivered to brain tissue when in the first mode.

In some embodiments, the controller comprises a first discrete controller and a second discrete controller. The first discrete controller can comprise a clinician-operated controller and the second discrete controller comprises a patient-operated controller. The clinician-operated controller and the patient-operated controller each can be configured to transition the stimulator from the first mode to the second mode. The clinician-operated controller can be further configured to transition the stimulator from the second mode to the first mode.

In some embodiments, the controller is configured to modify at least one of the first set of stimulation parameters or the second set of stimulation parameters. The controller can be configured to modify both the first set of stimulation parameters and the second set of stimulation parameters.

In some embodiments, the system further comprises a diagnostic tool for measuring at least one patient parameter and producing diagnostic data representing the at least one measured patient parameter, and at least one of the first set of stimulation parameters or the second set of stimulation parameters are based on the diagnostic data.

In some embodiments, the system further comprises a diagnostic tool for measuring at least one patient parameter and producing diagnostic data representing the at least one measured patient parameter, and the stimulator transitions between the first mode and the second mode based on the diagnostic data.

In some embodiments, the system further comprises a diagnostic tool for measuring at least one patient parameter and producing diagnostic data representing the at least one measured patient parameter, and the diagnostic tool comprises a device selected from the group consisting of: heart rate monitor; EKG measurement device; oximeter; combined heart rate and oximeter device such as a pulse oximeter; blood pressure measurement device; neuronal activity measurement device; EEG measurement device; sleep measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations thereof.

In some embodiments, the brain tissue stimulated comprises at least a portion of the fornix. The brain tissue stimulated can further comprise non-fornix brain tissue.

In some embodiments, the brain tissue stimulated comprises brain tissue selected from the group consisting of: fornix; entorhinal cortex; hippocampus; anterior thalamic nucleus; amygdala; mammillary bodies; parahippocampal cortex; temporal neocortex; septal nuclei; nucleus basalis of Meynert; subcallosal or subgenual cingulate; ventral capsule; ventral striatum and combinations thereof.

In some embodiments, the brain tissue stimulated comprises brain tissue selected from the group consisting of: Papez Circuit; hippocampus; cingulate gyrus; fornix; a mammilothalamic tract; amygdala; hypothalamus; mammillary bodies; septal nuclei; temporal neocortex; the medial forebrain bundle; anterior and mediodorsal nuclei of the thalamus; the diagonal band of the Broca; temporal stem and temporal white matter; brainstem; nucleus basalis of Meynert; anterior thalamic nucleus; entorhinal cortex; rhinal cortex; periventricular zone; anterior thalamus; anterior insula; caudate; dorsal anterior cortex; dorsal cingulate; medial frontal cortex; nucleus accumbens; orbital frontal cortex; parietal region; periaqueductal gray area; posterior cingulate area; subcallosal area; subcallosal cingulate; subgenual cingulate; Brodmann area 10; Brodmann area 24; Brodmann area 25; Brodmann area 11/Brodmann area 10; Brodmann area 24b; Brodmann area 31; Brodmann area 32/Brodmann area 10; Brodmann area 32/Brodmann area 11; Brodmann area 39; Brodmann area 46; Brodmann area 46/Brodmann area 9; Brodmann area 47; Brodmann area 6; Brodmann area 9; ventral/medial prefrontal cortex area; ventral/medial white matter; dorsolateral prefrontal cortex; premotor cortex; ventrolateral prefrontal cortex; dorsal anterior cingulate caudate nucleus; frontal pole periaqueductal gray area; dorsolateral prefrontal area; subsingular cingulate; parahippocampal cortex; parahippocampal gyrus; ventral capsule; ventral striatum; and combinations thereof.

In some embodiments, the brain tissue stimulated does not comprise tissue selected from the group consisting of: hippocampal tissue; optical tract tissue; and combinations thereof.

In some embodiments, the brain tissue stimulated does not comprise tissue selected from the group consisting of: posterior hypothalmic area; ventral tegmental area; lateral hypothalamic area; anterior hypothalamic nucleus; paraventricular nucleus; dorsal medial hypothalamic nucleus; ventromedial hypothalamic nucleus; arcuate nucleus; lateral tuberal nucleus; medial preoptic nucleus; supraoptic nucleus; and combinations thereof.

In some embodiments, the stimulator further comprises an implantable stimulation lead constructed and arranged to receive the stimulation energy from the stimulator and comprising at least one stimulation element constructed and arranged to stimulate brain tissue.

In some embodiments, the system further comprises at least one energy delivery element configured to deliver stimulation energy to brain tissue. The stimulation energy delivered by the at least one stimulation element can comprise energy selected from the group consisting of: electromagnetic energy such as electrical energy and/or magnetic energy; light energy such as visible, ultraviolet and/or infrared light energy; sound energy such as subsonic, sonic or ultrasound energy; and combinations thereof.

In some embodiments, the system further comprises an imaging device configured to produce patient image information. The imaging device can comprise a device selected from the group consisting of: MRI; fMRI; X-ray; fluoroscope; Ct-Scanner; PET Scanner; Diffusion Tensor Imaging (DTI) device; ultrasound imaging device; standardized Low Resolution Brain Electromagnetic Tomography (sLORETA) device; MagnetoEncephalography (MEG); and combinations thereof. The system can further comprise at least one stimulation element, and the system can be configured to position the at least one stimulation element relative to the brain tissue to be stimulated based on the patient image information.

In some embodiments, the system is configured to treat at least one neurological disease and at least one neurological disorder.

In some embodiments, the system is configured to treat multiple neurological diseases.

In some embodiments, the system is configured to treat multiple neurological disorders.

In some embodiments, the system is configured to regulate the level of one or more neurotrophic factors and/or neurotransmitters.

In some embodiments, the system is configured to ameliorate cognitive decline associated with dementia.

In some embodiments, the patient has reduced integrity of white matter tracts innervating limbic structures as determined by fractional anisotropy maps using diffusion tensor imaging. The innervated limbic structures can comprise at least the fornix.

In some embodiments, the system is configured to achieve at least one of: treats memory impairment; improves memory function; treats cognitive function loss; reverses synaptic loss; improves cognitive function; reduces degradation of cognitive function; promotes neurogenesis in the hippocampus of the patient's brain; drives neurotrophin expression; regulates one or more biomarkers related to Alzheimer's Disease such as amyloid-beta, tau, and/or phosphorylated tau; regulates BDNF expression; increases neurotransmitter release such as acetylcholine; or improves glucose utilization in the temporal lobe, the parietal lobe or both lobes of the patient's brain.

In some embodiments, the stimulator comprises at least an implanted portion. The at least an implanted portion can comprise at least one electrode constructed and arranged to stimulate the brain tissue. The at least one electrode can comprise an electrode selected from the group consisting of: single component bipolar electrode; multiple unipolar electrodes; stacked contact electrodes; discrete electrodes; electrode strip; grid of electrodes; paddle electrode; high-density/high channel or lead count micro-electrodes; and combinations thereof. The at least one electrode can comprise at least one electrode positioned in brain tissue. The at least one electrode can comprise at least one electrode positioned proximate the fornix. The at least one electrode can comprise two electrodes constructed and arranged to be placed bilaterally about the fornix. The at least one electrode can comprise at least one electrode positioned in a location to cause stimulation of the fornix. The at least one electrode can comprise multiple electrodes. The at least one electrode can comprise an electrode constructed and arranged for monopolar delivery of electrical energy. The at least one electrode can comprise an electrode constructed and arranged for multipolar delivery of electrical energy. The at least an implanted portion can comprise an implanted stimulation element selected from the group consisting of: electrode such as one or more electrodes configured to deliver electrical stimulation energy; magnetic field delivery element; light delivery element such as a visible, ultraviolet or infrared light delivery element; optogenetic delivery element; sound delivery element such as a subsonic wave or ultrasound wave delivery element; agent delivery element such as a chemical or pharmaceutical agent delivery element; and combinations thereof. The system can further comprise an energy generating element constructed and arranged to deliver energy selected from the group consisting of: electromagnetic energy such as electrical energy and/or magnetic energy; light energy such as visible, ultraviolet and/or infrared light energy; sound energy such as subsonic, sonic or ultrasound energy; and combinations thereof. The at least an implanted portion can comprise an implanted signal generator.

In some embodiments, the stimulator comprises at least an external portion. The at least an external portion can comprise an external stimulation element. The external stimulation element can comprise an electromagnetic field generator. The external stimulation element can comprise a sound generator. The external stimulation element can comprise a light energy generator. The at least an external portion can comprise an electrical signal generator. The stimulator can further comprise an implanted stimulation element electrically connected to the electrical signal generator. The implanted stimulation element can comprise at least one electrode.

In some embodiments, the stimulator comprises an implanted portion and an external portion.

In some embodiments, the stimulator is configured to stimulate tissue with electrical stimulation.

In some embodiments, the stimulator is configured to stimulate tissue with a stimulation energy selected from the group consisting of: electrical stimulation; magnetic stimulation; optical stimulation such as visible, ultraviolet or infrared light stimulation; sound stimulation such as ultrasound or subsonic wave stimulation; chemical stimulation such as stimulation from a drug or other agent; and combinations thereof.

In some embodiments, the stimulator is configured to stimulate the brain tissue in a continuous stimulation mode.

In some embodiments, the stimulator is configured to stimulate the brain tissue in a cyclical stimulation mode.

In some embodiments, the stimulator is further configured to stimulate non-brain tissue. The non-brain tissue can comprise non-brain nerve tissue. The non-brain tissue can comprise non-brain organ tissue. The non-brain tissue can comprise tissue selected from the group consisting of: vagus nerve; trigeminal nerve; carotid sinus; spinal cord; dorsal root ganglia; tibial nerve; sacral nerve; gastric nerve; and combinations thereof.

In some embodiments, the system further comprises an operator activatable switch, and the stimulator transitions from the first mode to the second mode when the switch is activated. The stimulator can transition back to the first mode after a predetermined period of time. Alternatively, the stimulator can transition back to the first mode when the switch is released.

In some embodiments, the stimulator is configured to provide monopolar stimulation in the first mode and bipolar stimulation in the second mode.

In some embodiments, the system is configured to increase and/or maintain glucose metabolism. In these embodiments, the stimulator can be configured to stimulate the fornix.

In some embodiments, the system is configured to increase and/or maintain one or more portions of hippocampal volume. In these embodiments, the stimulator can be configured to stimulate the fornix.

In some embodiments, the system is configured to increase blood flow of the hippocampus, increase angiogenesis and/or promote trophic release of endothelial growth factor, BDNF and/or a neuroprotective agent.

In some embodiments, the system is configured to cause neurogenesis. The system can be configured to cause hippocampal neurogenesis.

In some embodiments, the stimulator is configured to stimulate in the first mode when the patient is in a first state of sleep and to stimulate in the second mode when the patient is in a second state of sleep, wherein the first state of sleep is different than the second state of sleep.

According to another aspect of the present inventive concepts, a method of treating a patient is provided. The method comprises providing a stimulator for stimulating brain tissue; providing a controller for setting stimulation parameters of the stimulator; and operating the stimulator in a first mode with a first set of stimulation parameters and subsequently in a second mode with a second set of stimulation parameters different than the first set of stimulation parameters. The method is configured to treat at least one of a cognitive disease or a cognitive disorder.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

DETAILED DESCRIPTION OF THE INVENTION

Figure 1:
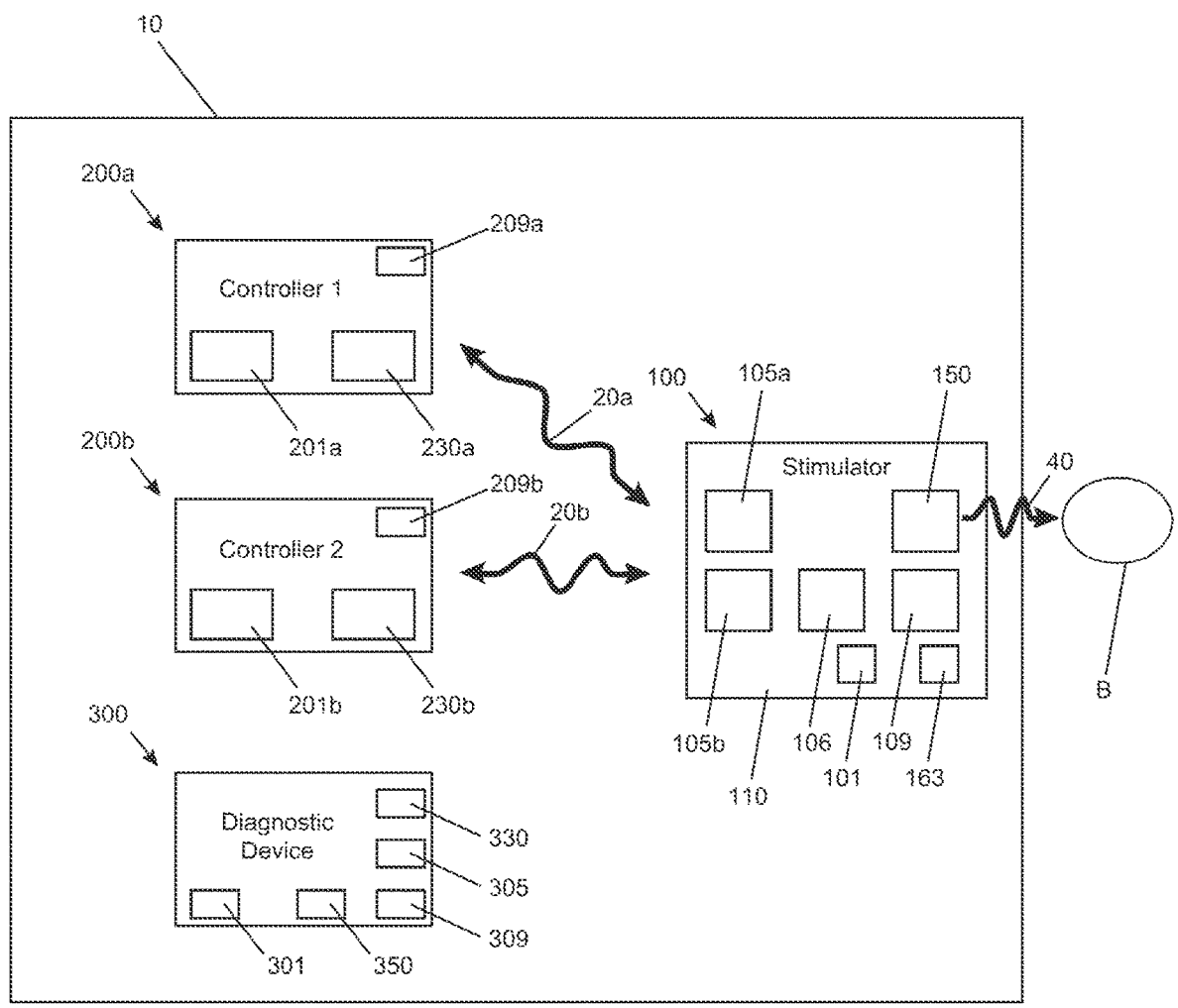
FIG. 1 illustrates a schematic view of a system for stimulating one or more portions of a patient's brain, consistent with the present inventive concepts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The systems of the present inventive concepts comprise a stimulator for stimulating brain tissue, and one or more controllers for setting stimulation parameters of the stimulator. The stimulator can be configured to operate in a first mode with a first set of stimulation parameters and in a second mode with a second set of stimulation parameters different than the first set of stimulation parameters. In some embodiments, the stimulator is configured to operate in three or more modes correlating to three or more sets of different stimulation parameters. The systems can be configured to transition between any two or more of the modes in repeating or non-repeating patterns.

The systems, devices and methods of the present inventive concepts are applicable to treat a patient, such as to treat one or more cognitive diseases or disorders of a patient. The cognitive diseases or disorders can include but are not limited to: Alzheimer's Disease (AD) such as Mild or Moderate Alzheimer's Disease; probably Alzheimer's Disease; a genetic form of Alzheimer's Disease; Mild Cognitive Impairment (MCI); hippocampal damage such as hippocampal damage due to Alzheimer's disease, anoxia, epilepsy, depression, post-traumatic stress disorder (PTSD) or traumatic brain injury (TBI); neuronal loss; neuronal damage; chemotherapy induced memory impairment; epilepsy; a seizure disorder; dementia; amnesia; a memory disorder such a spatial memory disorder; cognitive impairment associated with Schizophrenia; Parkinson's Disease related cognitive impairment or dementia; and combinations of these. Additionally or alternatively, the patient can be selected to treat negative symptoms of a disease or disorder selected from the group consisting of: schizophrenia; depression; post-traumatic stress disorder (PTSD); traumatic brain injury (TBI); other conditions of reversible impaired memory or cognition; and combinations of these.

In some embodiments, the patient is selected for treatment as described in applicant's co-pending U.S. application Ser. No. 13/655,652, entitled "Deep Brain Stimulation of Memory Circuits in Alzheimer's Disease", filed Oct. 19, 2012, the content of which is incorporated herein by reference in its entirety.

As used herein, the term "wired pathway" shall refer to an energy and/or information transmission pathway including a physical conduit such as a flexible conduit comprising: one or more wires; one or more optical (e.g. light transmitting) fibers; one or more fluid delivery tubes; one or more sound propagation guides; and combinations of these.

As used herein, the term "wireless" or "wireless pathway" shall refer to an energy and/or information transmission pathway that does not include or otherwise rely on a physical conduit for transmission, such as an electromagnetic, sound and/or light transmission of energy and/or information that passes through the tissue of a patient without the use of a physical conduit.

As used herein, the term "memory event" comprises one or more events in the patient's life experiences, such as one or more events that can be routinely recalled in a patient that does not suffer from a memory-related disease or disorder such as Alzheimer's Disease.

As used herein, the term "memory recall effect" shall refer to an effect that increases the likelihood of a patient to recall a memory event.

As used herein, the term "set of stimulation parameters" comprises one or more stimulation parameters used by a stimulator of the present inventive concepts to regulate stimulation (e.g. stimulation energy) delivered to tissue such as brain tissue.

Referring now to FIG. 1, a system for stimulating a patient's brain is illustrated, consistent with the present inventive concepts. System 10 includes stimulator 100 and one or more controllers, such as controller 200a and controller 200b (singly or collectively controller 200). In some embodiments, system 10 further includes diagnostic tool 300. System 10 can be constructed and arranged to treat a neurological disease, a neurological disorder and/or another patient disease or disorder, as described in detail herein. Stimulator 100 is configured to stimulate tissue, such as to stimulate at least a portion of a patient's brain B, such as via pathway 40. Controller 200 is configured to initiate and/or adjust (hereinafter "set" or "setting") one or more stimulation parameters 105 of stimulator 100. Controller 200a can be configured to communicate with stimulator 100 via pathway 20a. Controller 200b can be configured to communicate with stimulator 100 via pathway 20b.

Diagnostic tool 300 can be constructed and arranged to measure one or more patient parameters, and to produce diagnostic data 305 representing the measured patient parameters. The measuring of diagnostic data 305 by diagnostic tool 300 can include but is not limited to performing a data measurement function selected from the group consisting of: recording; gathering; assessing; collecting; determining; processing; combining; and combinations of these. In some embodiments, diagnostic tool 300 communicates with stimulator 100 and/or controller 200 via one or more wired or wireless pathways, not shown but configured similar to pathways 20a and/or 20b, such as to transfer diagnostic data 305 and/or one or more stimulation parameters 105 between diagnostic tool 300 and stimulator 100 and/or a controller 200. In some embodiments, diagnostic tool 300 provides diagnostic data 305 and/or one or more stimulation parameters 105 to an operator of system 10, such as via user interface 301.

In some embodiments, stimulator 100 is constructed and arranged similar to stimulator 100 of FIG. 3 described hereinbelow. In some embodiments, system 10 is used as described in reference to the method of FIG. 2 herein below. In some embodiments, system 10 is constructed and arranged to treat a neurological disease and/or disorder selected from the group consisting of: probable Alzheimer's Disease; a genetic form of Alzheimer's Disease; Mild Cognitive Impairment; hippocampal damage such as hippocampal damage due to Alzheimer's Disease, anoxia, epilepsy or depression; dementia; amnesia; a memory disorder such as a spatial memory disorder; cognitive impairment associated with Schizophrenia; Parkinson's Disease related cognitive impairment or dementia; neuronal loss; neuronal damage; chemotherapy induced memory impairment; epilepsy; seizure disorder; post-traumatic stress disorder (PTSD); traumatic brain injury (TBI); and combinations of these. In some embodiments, system 10 is constructed and arranged to treat multiple neurological diseases, multiple neurological disorders and/or at least one neurological disease and at least one neurological disorder.

One or more stimulation parameters 105 can be determined or otherwise set based on diagnostic data 305 produced by diagnostic tool 300. In some embodiments, stimulation parameters are set as described in applicant's co-pending application International PCT Patent Application Serial Number PCT/US2014/060923, titled "Brain Stimulation System including Diagnostic Tool", filed Oct. 16, 2014, the content of which is incorporated herein by reference in its entirety. Stimulation parameters 105 can comprise a first set of stimulation parameters 105*a* for operation of system 10 in a first mode of stimulation, and a second set of stimulation parameters 105*b* for operation of system 10 in a second mode of stimulation. In some embodiments, three or more sets of stimulation parameters 105 are used, such that system 10 can stimulate brain B in three or more modes of stimulation. In some embodiments, stimulator 100 is configured to deliver multiple modes of stimulation as is described herein below in reference to FIG. 2. In some embodiments, stimulator 100 or another component of system 10 includes algorithm 106 which can be configured to determine when stimulator 100 should transition between two or more modes of stimulation, such as between a first mode of stimulation and a second mode of stimulation, and vice versa.

Stimulator 100 includes stimulation element 150 comprising one or more stimulation elements such as electrodes or other energy delivery elements described in detail herein. One or more stimulation elements 150 are positioned (e.g. implanted and/or external to the patient) to stimulate one or more portions of brain B, such as to stimulate the fornix and/or another volume of brain B tissue. In some embodiments, stimulator 100 and one or more stimulation elements 150 are constructed and arranged to stimulate brain tissue selected from the group consisting of: fornix; entorhinal cortex; hippocampus; anterior thalamic nucleus; amygdala; mammillary bodies; parahippocampal cortex; temporal neocortex; septal nuclei; nucleus basalis of Meynert; subcallosal or subgenual cingulate; ventral capsule; ventral striatum and combinations of these. In some embodiments, stimulator 100 and one or more stimulation elements 150 are constructed and arranged to stimulate brain tissue selected from the group consisting of: Papez Circuit; hippocampus; cingulate gyrus; fornix; a mammillothalamic tract; amygdala; hypothalamus; mammillary bodies; septal nuclei; temporal neocortex; the medial forebrain bundle; anterior and mediodorsal nuclei of the thalamus; the diagonal band of the Broca; temporal stem and temporal white matter; brainstem; nucleus basalis of Meynert; anterior thalamic nucleus; entorhinal cortex; rhinal cortex; periventricular zone; anterior thalamus; anterior insula; caudate; dorsal anterior cortex; dorsal cingulate; medial frontal cortex; nucleus accumbens; orbital frontal cortex; parietal region; periaqueductal gray area; posterior cingulate area; subcallosal area; subcallosal cingulate; subgenual cingulate; Brodmann area 10; Brodmann area 24; Brodmann area 25; Brodmann area 11/Brodmann area 10; Brodmann area 24b; Brodmann area 31; Brodmann area 32/Brodmann area 10; Brodmann area 32/Brodmann area 11; Brodmann area 39; Brodmann area 46; Brodmann area 46/Brodmann area 9; Brodmann area 47; Brodmann area 6; Brodmann area 9; ventral/medial prefrontal cortex area; ventral/medial white matter; dorsolateral prefrontal cortex; premotor cortex; ventrolateral prefrontal cortex; dorsal anterior cingulate caudate nucleus; frontal pole periaqueductal gray area; dorsolateral prefrontal area; subsingular cingulate; parahippocampal cortex; parahippocampal gyrus; ventral capsule; ventral striatum; and combinations of these.

In some embodiments, stimulator 100 and one or more stimulation elements 150 are constructed and arranged to avoid directly and/or indirectly stimulating tissue selected from the group consisting of: hippocampal tissue; optical tract tissue; and combinations of these. In some embodiments, stimulator 100 and one or more stimulation elements 150 are constructed and arranged to avoid stimulation of posterior hypothalmic area; ventral tegmental area; lateral hypothalmic area; anterior hypothalamic nucleus; paraventricular nucleus; dorsal medial hypothalamic nucleus; ventromedial hypothalamic nucleus; arcuate nucleus; lateral tuberal nucleus; medial preoptic nucleus; supraoptic nucleus; and combinations of these.

Stimulator 100 can comprise one or more batteries, capacitors, and/or other electrical power supplies, such as power supply 163 shown. In some embodiments, stimulation parameters 105*a* require different amount of power during stimulation than stimulation parameters 105*b* require, such that battery life of stimulator 100 can be increased by using stimulation parameters associated with the lower power requirement. For example, stimulation parameters 105*b* can require more power than stimulation parameters 105*a*, and stimulation parameters 105*b* can be used for a limited time period, such as only when the patient is performing a specific task or having difficulty in recalling one or more memory events. In some embodiments, stimulation parameters 105*a* require minimal or no power (e.g. minimal or no stimulation energy is delivered).

In some embodiments, stimulation parameters 105*b* are configured to provide an improved memory recall effect than can be achieved with stimulation parameters 105*a*, such as when the stimulation parameters 105*b* deliver more energy to tissue than stimulation parameters 105*a* and/or stimulate more and/or different tissue than stimulation parameters 105*a*.

In some embodiments, stimulation parameters 105*a* deliver a different form of stimulation energy than the stimulation energy delivered using stimulation parameters 105*b*. In these embodiments, the difference in energy form can represent a difference in energy type, such as an energy type selected from the group consisting of: electrical energy; magnetic field energy; light energy; energy configured to optogenetically control neurons; sound energy; chemical energy; and combinations of these. Alternatively or additionally, the difference in energy form can represent a difference in the magnitude of energy delivered, such as a difference in magnitude delivered over time, difference in average magnitude delivered and/or difference in peak magnitude delivered. In these embodiments, the difference in magnitude can be at least 5%, 10%, 25%, 50% or 100%. The difference in energy delivered can comprise a difference in an energy delivery parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; and combinations of these.

In some embodiments, a difference in energy delivered between stimulation parameters 105*a* and 105*b* can comprise a difference in an energy delivery parameter selected from the group consisting of: voltage level; average voltage level; peak voltage level; current level; average current level; peak current level; power level; average power level; peak power level; frequency; phase; duty cycle; pulse width; modulation; and combinations of these. In these embodiments, at least one of the stimulation parameters 105*a* and/or 105b can comprise a duty cycle of approximately 1% and/or an "on time" within each duty cycle of approximately 90 μseconds.

In some embodiments, stimulation element 150 is configured to deliver at least light energy, and the difference in light energy delivered between stimulation parameters 105a and 105b can comprise a difference in a light energy delivery parameter selected from the group consisting of: intensity; average intensity; peak intensity; power level; average power level; peak power level; frequency; phase; pulse width; modulation; and combinations of these.

In some embodiments, stimulation element 150 is configured to deliver at least sound energy, and the difference in sound energy delivered between stimulation parameters 105a and 105b can comprise a difference in a sound energy delivery parameter selected from the group consisting of: intensity; average intensity; peak intensity; power level; average power level; peak power level; frequency; phase; pulse width; modulation; and combinations of these.

In some embodiments, stimulation element 150 is configured to deliver at least one or more agents, and the difference in agent delivery between stimulation parameters 105a and 105b can comprise a difference in an agent delivery parameter selected from the group consisting of: agent delivery rate; flow rate; concentration of agent being delivered; and combinations of these.

In some embodiments, stimulation element 150 comprises a first stimulation element and a second stimulation element (e.g. two different electrodes or two different sets of electrodes) and the first stimulation element delivers energy in the first mode of stimulation (i.e. as determined by the stimulation parameters 105a) and the second stimulation element delivers energy in the second mode of stimulation (i.e. as determined by the stimulation parameters 105b). In these embodiments, the second mode of stimulation can include delivery of energy by both the first and second stimulation elements 150 (e.g. when only the first stimulation element delivers energy in the first mode of stimulation). Alternatively, the first mode of stimulation can include delivery of energy by only the first stimulation element (e.g. a set of one or more electrodes) and the second mode of stimulation can include delivery of energy by only the second stimulation element (e.g. a set of a different one or more electrodes). In these embodiments, the first and second stimulation elements 150 can be positioned on a single lead or multiple leads, such that the transition between the first mode of stimulation and the second mode of stimulation results in stimulation from the same (single) lead or different leads, respectively.

In some embodiments, the first mode of stimulation (as determined by the stimulation parameters 105a) is associated with less energy drain from power supply 163 than the energy drain that occurs during the second mode of stimulation (as determined by the stimulation parameters 105b). In other words, the power required during the second mode is greater than the power required in the first mode. In these embodiments, use of the second mode can be limited to specific patient memory recall and/or patient task events such as to increase battery life of stimulator 100 (e.g. to increase implant life of an implanted portion of stimulator 100). In these embodiments, the first set of stimulation parameters 105a can comprise a parameter with a lower value than a corresponding parameter in the second set of stimulation parameters 105b, wherein the first stimulation parameter comprises a parameter selected from the group consisting of: average energy delivered; cumulative energy delivered; peak energy delivered; duty cycle for energy delivery; voltage of energy delivered; current of energy delivered; intensity of energy delivered; and combinations of these.

In some embodiments, the tissue stimulated in the first mode of stimulation comprises a first volume of tissue of brain B, and the tissue stimulated in the second mode of stimulation comprises a second volume of tissue of brain B, wherein at least a portion of the second volume of tissue of brain B is not included in the first volume of tissue of brain B. In these embodiments, the second volume of tissue of brain B can comprise a larger volume than the first volume of tissue of brain B. In some embodiments, the second volume of tissue of brain B can comprise all of the first volume of tissue of brain B.

Stimulator 100 can be configured to stimulate with the first set of stimulation parameters 105a for multiple discrete first time periods and to stimulate with the second set of stimulation parameters 105b for multiple discrete second time periods. In some embodiments, stimulator 100 is configured to repeatedly alternate between stimulating with the first set of stimulation parameters 105a and the second set of stimulation parameters 105b. In some embodiments, all of the first time periods comprise similar durations of time. In some embodiments, all of the second time periods comprise similar durations of time. In some embodiments, transitioning to the second mode of stimulation can be triggered by an event, such as a patient event. The patient event can comprise an event selected from the group consisting of: inability to recall a memory event; inability to access a memory engram; frustration; anger; disorientation; and combinations of these. The patient event can comprise an event detected by sensor 109 or another sensor of system 10 (hereinafter sensor 109), such as a sensor selected from the group consisting of: electrode; neuronal activity sensor; EEG sensor; polysomnography (PSG) sensor; sleep sensor; sleep state sensor; local field potential sensor; neurochemical sensor; EKG sensor; pH sensor; pressure sensor; blood pressure sensor; respiration sensor; acoustic sensor; optical sensor; blood gas sensor; blood glucose sensor; glucose sensor; insulin sensor; blood oxygen sensor; eye movement sensor; blink rate sensor; magnetic sensor; strain gauge; temperature sensor; and combinations of these. The patient event can comprise activation of a switch (e.g. activation by the patient, clinician or other operator of system 10), such as a switch of user interface 201a of controller 200a and/or user interface 201b of controller 200b. In some embodiments, at least one of the first time periods comprises a different duration of time than another first time period. In some embodiments, at least one of the second time periods comprises a different duration of time than another second time period. In some embodiments, each first time period comprises at least 5 minutes and each second time period comprises at least 30 seconds. In some embodiments, each first time period comprises at least 1 hour and each second time period comprises at least 30 seconds. In some embodiments, each first time period comprises at least 24 hours and each second time period comprises at least 30 seconds. In some embodiments, each first time period comprises at least 5 minutes and each second time period comprises at least 5 minutes. In some embodiments, each first time period comprises at least 1 hour and each second time period comprises at least 5 minutes. In some embodiments, each first time period comprises at least 24 hours and each second time period comprises at least 5 minutes. In some embodiments, stimulator 100 is configured to deliver more power (e.g. more current) during each second time period than the power delivered during each first time period. In these embodiments, stimulator 100 can be configured to deliver minimal or no energy during each first time period.

Stimulator 100 can be configured to transition between two stimulation modes (e.g. from the first mode to the second mode, from the second mode to the first mode and/or from any mode to a different mode) based on detection of an event (e.g. duration of stimulation in a mode, time of day, patient environment state change and/or patient event) or detection of a condition (e.g. patient environment condition and/or patient condition). In some embodiments, stimulator 100 is configured to transition between modes based on an elapsed time (duration) within a mode. In some embodiments, algorithm 106 of stimulator 100 and/or another algorithm of system 10 (hereinafter algorithm 106) determines when stimulator 100 transitions between stimulation modes. In these embodiments, algorithm 106 can determine whether a transition between modes should occur based on information received from sensor 109, controller 200 and/or diagnostic device 300.

In some embodiments, when stimulator 100 has operated in the first mode of stimulation for a pre-determined time period, a transition to the second mode of stimulation occurs (e.g. the transition automatically occurs as determined by algorithm 106 comprising an electronic timer). In some embodiments, when the stimulator has operated in the second mode of stimulation for a pre-determined time period, a transition to the first mode occurs (e.g. the transition automatically occurs as determined by algorithm 106 comprising an electronic timer).

In some embodiments, stimulator 100 transitions between the first mode of stimulation and the second mode of stimulation based on the time of day (e.g. when stimulator 100 and/or algorithm 106 comprises an electronic clock). In some embodiments, stimulator 100 operates in the second mode for at least a portion of the nighttime and stimulator 100 operates in the first mode for at least a portion of the daytime. In these embodiments, the power delivered in the second mode can be greater than or less than the power delivered in the first mode (i.e. more or less power, respectively, delivered at night).

In some embodiments, stimulator 100 transitions between the first mode of stimulation and the second mode of stimulation based on a patient parameter (e.g. a patient parameter whose value is monitored by algorithm 106). In these embodiments, the transition can occur due to a change in the patient parameter and/or when the patient parameter exceeds a threshold (e.g. rises above a maximum threshold, falls below a minimum threshold and/or falls outside of a range of values). Sensor 109 can be configured to produce a signal related to the patient parameter. Algorithm 106 can be configured to assess the signal from sensor 109 and determine if the parameter has changed (e.g. significantly changed) and/or exceeded a threshold. In some embodiments, the patient parameter comprises a circadian rhythm parameter of the patient. In some embodiments, the patient parameter comprises a patient awakeness parameter, such as when stimulator 100 transitions to the second mode of stimulation when the patient falls asleep (e.g. when the second mode is associated with more or less energy being delivered than is delivered in the first mode). In these embodiments, sensor 109 can be configured to produce a signal related to patient awakeness and algorithm 106 can assess the signal provided by sensor 109 to determine if the patient is asleep or awake. In some embodiments, sensor 109 is configured to produce a signal related to a patient's state of sleep, and stimulator 100 can transition between modes when the patient's state of sleep changes (e.g. when sensor 109 is an EEG or other sensor that produces a signal related to the patient's sleep state).

In some embodiments, the patient parameter causing the transition comprises a patient activity level parameter, such as when stimulator 100 transitions between the first and second modes of stimulation when the patient activity level exceeds a threshold. In these embodiments, sensor 109 can comprise a sensor configured to produce a signal related to patient activity level and algorithm 106 can assess the signal provided by sensor 109 to determine if the patient activity level has changed (e.g. significantly changed) and/or exceeded a threshold (e.g. when the second mode is associated with more or less energy being delivered than is delivered in the first mode).

In some embodiments, the patient parameter causing the transition comprises a patient activity parameter, such as when stimulator 100 transitions between the first and second modes of stimulation when a particular patient activity is detected, such as a patient activity selected from the group consisting of: reading, writing; talking; participating in a conversation; and combinations of these. In these embodiments, sensor 109 can comprise a sensor configured to produce a signal related to a patient activity and algorithm 106 can assess the signal provided by sensor 109 to determine if the patient activity is occurring.

In some embodiments, the patient parameter causing the transition comprises a patient physiologic parameter, such as when stimulator 100 transitions between the first and second modes of stimulation when the patient physiologic parameter changes and/or exceeds a threshold. In these embodiments, the patient physiologic parameter can comprises a parameter selected from the group consisting of: blood pressure; heart rate; eye movement; blink rate; respiration; a glucose level; an insulin level; a theta rhythm state; a sleep state; one or more brain signals; one or more heart signals; and combinations of these. In these embodiments, sensor 109 can comprise a sensor configured to produce a signal related to the patient physiologic parameter and algorithm 106 can assess the signal provided by sensor 109 to determine if the patient physiologic parameter has changed (e.g. significantly changed) and/or exceeded a threshold.

In some embodiments, the patient parameter causing the transition comprises a parameter related to the patient's ability to recall a memory event, such as when stimulator 100 transitions between the first and second modes of stimulation when the patient is unable to recall a memory event. In these embodiments, inability to recall a memory event can result in transition from the first mode of stimulation to the second mode of stimulation, such as when the first mode of stimulation delivers minimal or no energy to brain B tissue and/or when the second mode of stimulation delivers more power to brain B tissue than the first mode of stimulation. Algorithm 106 can be configured to detect the patient's inability to recall a memory event (e.g. when the patient activates controller 200 and/or sensor 109 detects patient agitation or frustration and/or is otherwise configured to detect the patient's inability to recall a memory event). Algorithm 106 can comprise one or more biases, such as a bias towards false positives (i.e. false detections of inability to recall a memory event). Algorithm 106 can be configured to assess signals provided by sensor 109 and to compare the assessment to one or more thresholds, such as when algorithm 106 and/or a threshold are biased toward false positives.

In some embodiments, stimulator 100 is configured to transition between the first and second modes of stimulation when an operator action occurs, such as an action of an operator selected from the group consisting of: the patient; a clinician; a healthcare provider; a family member; and combinations of these. Stimulator 100, controller 200 and/or another component of system 10 can comprise a switch configured to cause the transition between the first and second modes of stimulation. In some embodiments, the patient activates the switch (e.g. user interface 201 of controller 200) when the patient is unable to recall a memory event and/or desires to recall one or more memory events.

As described above, sensor 109 can be configured to produce a signal used to determine (e.g. by algorithm 106) if stimulator 100 should transition between first and second modes of stimulation. Algorithm 106 can be biased, such as a bias towards false positives that results in additional stimulation energy being delivered or other effect of a transition between the first and second modes of stimulation. Sensor 109 and/or algorithm 106 can be configured to determine when the patient is awake and asleep, such as to change modes based on the level of awakeness. Sensor 109 can comprise a sensor selected from the group consisting of: electrode; neuronal activity sensor; EEG sensor; polysomnography (PSG) sensor; sleep sensor; sleep state sensor; local field potential sensor; neurochemical sensor; EKG sensor; pH sensor; pressure sensor; blood pressure sensor; respiration sensor; acoustic sensor; optical sensor; blood gas sensor; blood glucose sensor; glucose sensor; insulin sensor; blood oxygen sensor; eye movement sensor; blink rate sensor; magnetic sensor; strain gauge; temperature sensor; and combinations of these.

Stimulator 100 can be configured to transition between different modes of stimulation based on a trigger event. In some embodiments, stimulator 100 transitions from the first mode of stimulation to the second mode of stimulation upon a trigger event. Subsequently, stimulator 100 can transition from the second mode of stimulation back to the first mode of stimulation after a pre-determined period of time, such as a time of less than four hours or less than one hour. Applicable trigger events include but are not limited to: operator activation of a switch; a patient event; a patient physiologic event; a patient event detected by a sensor; and combinations of these. The second mode of stimulation can deliver more power than the first mode, such as when the first mode of stimulation delivers minimal or no power to brain B tissue.

As described hereinabove, controllers 200a and/or 200b can comprise a switch (e.g. a switch of user interface 201a and/or 201b, respectively) that causes stimulator 100 to transition between the first stimulation mode (using first stimulation parameters 105a) and the second stimulation mode (using second stimulation parameters 105b). In some embodiments, the switch can cause a transition from the first stimulation mode to the second stimulation mode, but not from the second stimulation mode to the first stimulation mode (or vice versa). In these embodiments, the transition back to the previous mode can be caused by a different trigger event and/or automatically, after a pre-determined time duration, such as when the second mode of stimulation is performed at a higher power than the first mode of stimulation, and the second mode automatically transitions to the first mode after the pre-determined time duration. In some embodiments, stimulator 100 transitions from the first mode of stimulation to the second mode of stimulation when the switch is activated, and remains in the second mode of stimulation until the switch is released and/or a pre-determined time period is achieved.

In some embodiments, controller 200a is configured for use by a clinician and/or other caregiver and controller 200b is configured for use by the patient and/or a patient family member. In these embodiments, controller 200a can be configured to transition from the first mode of stimulation to the second mode of stimulation and from the second mode of stimulation to the first mode of stimulation, while controller 200b is configured to transition from the first mode of stimulation to the second mode of stimulation, but not back again (e.g. when stimulator 100 is configured to transition back to the first mode from the second mode after a different trigger event and/or after a pre-determined time period occurs). In some embodiments, controller 200a and/or controller 200b can be configured to modify the first set of stimulation parameters 105a and/or the second set of stimulation parameters 105b, such as when controller 200b can modify a limited set of stimulation parameters 105 and controller 200a can modify a larger set of stimulation parameters 105.

Diagnostic tool 300 can be configured measure at least one patient parameter and produce diagnostic data 305 representing the at least one patient parameter. Stimulation parameters 105a and/or 105b can be determined using, or otherwise be based on, diagnostic data 305. In some embodiments, transition between the first stimulation mode (using stimulation parameters 105a) and the second stimulation mode (using stimulation parameters 105b) occurs based on diagnostic data 305. Diagnostic tool 300 can comprise a tool selected from the group consisting of: heart rate monitor; EKG measurement device; oximeter; combined heart rate and oximeter device such as a pulse oximeter; blood pressure measurement device; neuronal activity measurement device; EEG measurement device; sleep measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations of these.

Pathway 40 can comprise a wired or wireless pathway as described in detail herein. Stimulator 100 can comprise an implantable stimulator, an external (e.g. non-implanted) stimulator, or it can comprise both implantable and external portions. Controller 200a is configured to communicate with stimulator 100, via pathway 20a, such as to set one or more stimulation parameters 105 of stimulator 100. Controller 200b can also be configured to communicate with stimulator 100, via pathway 20b, such as to set one or more stimulation parameters 105 of stimulator 100. Pathways 20a and/or 20b (singly or collectively pathway 20) can comprise a wired or wireless pathway as described herein. Stimulator 100 can comprise a user interface 101, such as a user interface 101 positioned on an external portion of stimulator 100. User interface 101, and the other user interfaces of the present inventive concepts, can comprise one or more user input or user output components, such as a component selected from the group consisting of: switch; membrane switch; mouse; keyboard; microphone; a graphical and/or alphanumeric screen; touch screen; light; speaker or other audio transducer; vibrational or other tactile transducer; and combinations of these.

One or more components of system 10 can include another component of system 10, such as when one or more of at least a portion of stimulator 100, controller 200 and diagnostic tool 300 are combined (e.g. within a common housing). For example, at least a portion of stimulator 100 can comprise at least a portion of controller 200a and/or controller 200b, such as when stimulator 100 includes an external portion comprising user interface 101 which is configured to set one or more stimulation parameters 105. In some embodiments, at least a portion of stimulator 100 can comprise at least a portion of diagnostic tool 300, such as when stimulator 100 comprises one or more sensors 109 constructed and arranged to record one or more patient parameters, such as are described in detail herein. In some embodiments, one or more sensors 109 are further constructed and arranged to stimulate tissue such as brain B tissue. In some embodiments, at least a portion of controller 200 comprises at least a portion of diagnostic tool 300, such as when controller 200 comprises one or more sensors 209 (e.g. sensor 209a of controller 200a and/or sensor 209b of controller 200b, also as described in detail herein) constructed and arranged such that controller 200 can function as a heart rate monitor, a blood pressure monitor and/or another diagnostic tool configured to produce diagnostic data 305.

Stimulator 100 can comprise stimulation element 150, which can comprise one or more stimulation elements configured to generate and/or deliver energy to stimulate brain B or other tissue of a patient. In some embodiments, stimulation element 150 comprises two discrete stimulation elements, each configured to generate and/or deliver energy to stimulate brain B or other tissue of the patient. Alternatively or additionally, stimulation element 150 can comprise a stimulation energy generating element configured to produce energy to stimulate tissue. In some embodiments, a first stimulation element 150 comprises a stimulation generating element that delivers energy to a second stimulation element 150 configured as a stimulation delivery element, such as when the second stimulation element 150 comprises one or more electrodes which receive electrical energy from the first stimulation element 150.

In some embodiments, stimulation element 150 comprises one or more stimulation delivery elements selected from the group consisting of: electrode such as one or more electrodes configured to deliver electrical stimulation energy; magnetic field delivery element; light delivery element such as a visible, ultraviolet or infrared light delivery element; energy delivery element configured to optogenetically control neurons; sound delivery element such as a subsonic wave or ultrasound wave delivery element; agent delivery element such as a chemical or pharmaceutical agent delivery element; and combinations of these. Alternatively or additionally, stimulation element 150 can comprise one or more stimulation generating elements constructed and arranged to deliver a form of energy selected from the group consisting of: electromagnetic energy such as electrical energy and/or magnetic energy; light energy such as visible, ultraviolet and/or infrared light energy; sound energy such as subsonic, sonic or ultrasound energy; and combinations of these. Alternatively or additionally, stimulation element 150 can comprise an agent delivery pump or reservoir; such as a pump configured to deliver a chemical or pharmaceutical agent through one or more catheters or other fluid delivery conduits of stimulator 100.

Stimulator 100 can comprise one or more implanted components (e.g. one or more discrete or otherwise physically separated components), one or more components external to the patient's body, or both at least one implanted component and at least one external component. Stimulator 100 can comprise two or more components, such as two or more components connected with a physical cable including electrically conductive wires, optical fibers, sound guides and/or fluid delivery tubes, and/or two or more components which transmit and/or receive information via wireless transmission. In some embodiments, stimulator 100 is configured as is described in applicant's co-pending U.S. patent application Ser. No. 13/655,652, entitled "Deep Brain Stimulation of Memory Circuits in Alzheimer's Disease", filed Oct. 19, 2012, the content of which is incorporated herein by reference in its entirety.

Stimulator 100 can comprise at least one housing, such as housing 110. Housing 110 can surround electronic components, power supply 163 (e.g. one or more batteries), one or more stimulation elements 150, and/or other components such as those described in reference to FIG. 3 herein below. Housing 110 can be constructed and arranged for implantation in the patient or remain external. Housing 110 can comprise two or more discrete housings, such as two or more discrete housings surrounding different sets of internal components, such as a first housing constructed and arranged to be implanted in the patient and a second housing constructed and arranged to remain external to the patient.

In some embodiments, stimulator 100 comprises at least an implanted portion and a first stimulation element 150 (positioned within the implanted portion) comprises a signal generator, such as a signal generator constructed and arranged to deliver electrical and/or one or more other forms of energy to a second stimulation element 150. In these embodiments, energy generated by first stimulation element 150 can travel through a wired or wireless pathway 40 (e.g. a pathway that comprises one or more wires or other energy carrying conduits which pass under the skin from the chest to the brain) to deliver stimulating energy to one or more second stimulation elements 150. Second stimulation element 150 can be positioned on, in and/or proximate the patient's brain B and/or other tissue to be stimulated. In some embodiments, one or more second stimulation elements 150 can be positioned in a location selected from the group consisting of: a subdural location; a supradural location; on and/or in the skull; on and/or in the scalp; and combinations of these.

In some embodiments, stimulator 100 comprises at least an external portion and at least one stimulation element 150 is positioned in an external portion of stimulator 100. In these embodiments, an externally positioned stimulation element 150 can be configured to non-invasively deliver energy to tissue. For example, stimulation element 150 can comprise an electromagnetic field generator, a sound generator, a light energy generator and/or other energy generator configured to deliver energy non-invasively through the skin through a wireless pathway 40 (e.g. through the skin and skull of the patient) to stimulate one or more portions of brain B. Wireless stimulation transmissions can comprise a transmission selected from the group consisting of: electromagnetic waves; sound waves such as ultrasonic and subsonic waves; light waves; and combinations of these. Non-limiting examples of non-invasive stimulation devices include: one or more transcranial magnetic stimulation devices, such as is described in U.S. Pat. No. 7,087,008, entitled "Apparatus and Methods for Delivery of Transcranial Magnetic Stimulation", filed May 3, 2002, the content of which is incorporated herein by reference in its entirety; one or more external focused energy delivery devices, such as is described in U.S. patent application Ser. No. 13/169, 288, entitled "Systems and Methods for Stimulating Tissue Using Focused Energy", filed Jun. 27, 2011, the content of which is incorporated herein by reference in its entirety; ultrasound stimulation devices; optogenetics-based stimulation devices; light-based stimulation devices; fiber optic based stimulation devices; and combinations of these.

Pathway 40 can comprise one or more physical conduits such as wires, fluid delivery tubes, sound guides, and/or optical fibers that connect to one or more electrodes, agent delivery elements and/or other stimulation delivery elements 150 positioned in and/or proximate to a location within brain B or other tissue to be stimulated. Pathway 40 can include a first lead that is positioned to stimulate a specific site in brain B. In these embodiments, stimulation element 150 can comprise one or more electrodes positioned in the hypothalamic area in proximity to the fornix, and/or at a different location as described herein. Stimulator 100 can take the form of a fully implanted signal generator, such as a signal generator similar to signal generator Model 7424, manufactured by Medtronic, Inc. under the trademark Itrel II. Pathway 40 can comprise one or more forms, such as any of the leads compatible with the Model 7424 such as Model 3387 lead set, for stimulating brain B. The lead can be coupled to stimulator 100 by a compatible lead extension.

Controllers 200a and/or 200b can be configured to initiate, adjust and/or otherwise set at least one stimulation parameter 105, such as a stimulation parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; agent delivery rate; physiologic concentration; power of light delivered to tissue; frequency of light delivered to tissue; a modulation parameter of light delivered to tissue; amplitude of sound delivered to tissue; frequency of sound delivered to tissue; a modulation parameter of sound delivered to tissue; mass of agent delivered to tissue; volume of agent delivered to tissue; concentration of agent delivered to tissue; delivery rate of agent delivered to tissue; and combinations of these. System 10 stimulation parameters 105 can be set by signals sent from controller 200 to stimulator 100 via pathway 20.

In some embodiments, stimulation element 150 comprises up to four implanted stimulation electrodes, such as four electrodes implanted into a portion of brain B using conventional stereotactic surgical techniques. In some embodiments, stimulation element 150 comprises two or more electrodes spaced approximately 1.5 mm apart. Each of the up to four electrodes (stimulation elements 150) can be individually connected to stimulator 100 through pathway 40 which can include a first lead with conductors for each electrode. The first lead can be surgically implanted through a hole in the skull and the conductors can be implanted between the skull and the scalp. The lead with conductors can be electromechanically attached to stimulator 100. In some embodiments, at least a portion of stimulator 100 is implanted in a human body, for example in the chest, within an arm, and/or in the abdomen of a human body. In some embodiments, at least a portion of stimulator 100 is implanted in the chest and pathway 40 comprises set of conductors that is implanted subcutaneously along the head, neck and shoulder to connect a housing of the portion of stimulator 100 implanted in the chest. Pathway 40 can comprise twin leads, a first lead and a second lead. The first lead can comprise a first stimulation element 150 comprising one or more electrodes and the second lead can comprise a second stimulation element 150 comprising one or more electrodes. The first and second leads can be implanted into brain B bilaterally (e.g. bilaterally about the fornix of brain B), with each operably connected to a single stimulator 100 portion. Alternatively, the second lead can be supplied with stimulating energy from a separate stimulator 100 portion (e.g. a second portion implanted in the chest or other internal location of the patient). The stimulation elements 150 (e.g. electrodes) of the two stimulation leads can be positioned proximate two separate sets of nuclei, such as to potentiate each other's effects. In some embodiments, the first and second leads are positioned proximate two separate nuclei with opposite effects, with the stimulation delivered being used to fine-tune the response through opposing forces. It will be appreciated, however, that any number of electrodes or other stimulation elements 150 can be positioned within, on and/or proximate to brain B, remote from brain B, and/or external to the patient's body, in accordance with the present inventive concepts. Additionally, one or more secondary electrodes or other secondary stimulation elements 150 can be implanted or otherwise positioned so that a secondary stimulation portion lies in communication with another predetermined portion of brain B.

System 10 can be utilized in monopolar and/or multipolar electrical stimulation configurations (e.g. monopolar, bipolar and/or stimulation configurations including 3 or more poles). In some embodiments, system 10 delivers monopolar energy, such as when housing 110 and at least a portion of stimulator 100 are implanted in the patient, such that housing 110 can function as a lead (e.g. a positive lead). In these embodiments, stimulation element 150 can comprise one or more electrodes positioned in brain B, the one or more electrodes functioning as the associated lead (e.g. as negative leads). In some embodiments, one mode of stimulation (e.g. the first mode of stimulation including stimulation parameters 105a) comprises monopolar stimulation of brain B and a different mode of stimulation (e.g. the second mode of stimulation including stimulation parameters 105b) comprises a bipolar stimulation of brain B, and vice versa.

System 10 can be constructed and arranged to provide stimulation continuously and/or intermittently, such as for a chronic period of time of at least 1 month, at least 3 months or at least 6 months. In some cases, stimulation can be provided for a longer period of time such as 12 months or more. Intermittent stimulation can include delivery of constant or pulsed stimulation energy with stimulation "on" times of at least 30 minutes, or at least 60 minutes. In some embodiments, the constant or pulsed stimulation energy delivery duty cycle (ratio of "on" time to the sum of "on" time plus "off" time) ranges from 20% to 80%. Stimulation can be performed in either an open loop or closed loop mode. In some embodiments, stimulation is initiated and/or modified to achieve an acute goal (e.g. by a caregiver or the patient), such as to perform an acute task or activity in which a memory recall effect is desirable, such as can be caused by a transition between the stimulation modes of the present inventive concepts. Stimulation can comprise delivery of electrical energy, sound energy, chemical energy, light energy, and/or the delivery of a pharmaceutical drug or other agent. One or more stimulation elements 150 configured as electrodes can be of various forms selected from the group consisting of: single component bipolar electrode; multiple unipolar electrodes; stacked contact electrodes; discrete electrodes; electrode strip; grid of electrodes; paddle electrode; high-density/high channel or lead count micro-electrodes; and combinations of these.

Stimulator 100 can include an agent delivery mechanism, such as a mechanism including a pump and one or more catheters configured to deliver one or more agents to one or more brain B or other body locations. In some embodiments, system 10 is constructed and arranged to deliver both electrical stimulation and agent delivery, sequentially and/or simultaneously. In these embodiments, a pump can be implanted below the skin of the patient, such as when the pump has an access port into which a needle can be inserted through the skin to inject a quantity of a liquid agent, such as a medication or other drug. The liquid agent is delivered from the pump through a catheter (e.g. after traveling from a pumping chamber and through a catheter access port attached to the side of the pump), and into the patient. The catheter can be positioned to deliver the agent to one or more specific infusion sites of brain B. The pump can take the form of any number of known implantable pumps including for example that which is disclosed in U.S. Pat. No. 4,692,147, "Drug Administration Device", the content of which is incorporated herein by reference in its entirety. The distal end of the catheter can terminate in a cylindrical hollow tube having a distal end implanted, such as by conventional stereotactic surgical techniques, into a portion of brain B to affect tissue within the human brain. The tube can be surgically implanted through a hole in the skull and the catheter can be implanted between the skull and the scalp, with the catheter fluidly attached to the pump. The pump can be implanted in a subcutaneous pocket located in the chest below the clavicle. Alternatively, the pump can be implanted in the abdomen. The catheter can be divided into twin tubes (e.g. two separate catheters attached to a single pump or a single catheter with two lumens) that have their distal portions implanted into brain B in bilateral locations. Alternatively, a second catheter can be implanted on the other side of brain B and can be supplied with drugs or other stimulating agents from a separate pump. The pump can be programmed to deliver one or more agents according to a particular dosage and/or time interval. For example, the pump can deliver drug therapy over a first period with a high dose configured to induce a high level of neurogenesis, after which a lower dose is delivered to maintain neurogenesis and secondary trophic effects (e.g. axonal sprouting and synaptogenesis). Any number of neurotrophins or drugs that stimulate neurons can be administered including, but not limited to: NGF; BDNF; NT-3; FGF; EGF; GDNF; Neurturin; Artemin; Persephin; and combinations of these.

System 10 can be constructed and arranged to modulate memory circuits to produce clinical benefits, such as to modulate memory circuits in the brain B to reduce the progression of or otherwise treat the effects of Alzheimer's Disease (AD). System 10 can modulate memory circuits in brain B via electrical or other stimulation means as described in detail herein. System 10 can be constructed and arranged to stimulate brain tissue selected from the group consisting of: fornix; entorhinal cortex; hippocampus; anterior thalamic nucleus; amygdala; mammilary bodies; parahippocampal cortex; temporal neocortex; septal nuclei; nucleus basalis of Meynert; subcallosal or subgenual cingulate; ventral capsule; ventral striatum; and combinations thereof. The stimulation site within one or more locations of brain tissue can be used to stimulate, activate or otherwise affect one or more similar or different brain tissue locations, such as a stimulation configured to affect a brain location selected from the group consisting of: fornix; hippocampus; parahippocampal gyrus; entorhinal cortex; amygdale; mammillary bodies; parahippocampal cortex; temporal neocortex; septal nuclei; nucleus basalis of Meynert; subcallosal or subgenual cingulate; and combinations of these. Alternatively or additionally, system 10 and one or more stimulation elements 150 can be constructed and arranged to stimulate non-brain tissue, such as nerve or organ tissue separate from the brain. Stimulated tissue can comprise tissue selected from the group consisting of: vagus nerve; trigeminal nerve; carotid sinus; spinal cord; dorsal root ganglia; tibial nerve; sacral nerve; gastric nerve; and combinations thereof. In some embodiments, system 10 is constructed and arranged to stimulate at least a portion of the hypothalamus, such as at least a portion of the fornix. The fornix is a large axonal bundle that constitutes a major inflow and output pathway from the hippocampus and medial temporal lobe. The hippocampus is a critical component of the limbic circuitry and is distinguished among some of the regions of the brain by persistent production of new neurons. The fornix is involved in memory formation and is known to be affected early in the progression of AD. In some embodiments, loss of fornix integrity associated with hippocampal volume loss can be detected by diagnostic tool 300 and used by system 10 to predict the progression of AD.

System 10 can be constructed and arranged to sustain and/or improve the function of the fornix. Alternatively or additionally, system 10 can be constructed and arranged to therapeutically affect the hippocampus and/or cortical circuits (e.g. the cortico-cortico circuits). Stimulation of the fornix by system 10 can be used to activate the hippocampus and cortical regions in brain B's default network, a network of brain regions that are active when the individual is not focused on the outside world and/or the brain is at wakeful rest. Patients with AD can exhibit a decrease in glucose metabolism over time. System 10 can be constructed and arranged to increase or maintain (e.g. prevent the decrease of) glucose metabolism, such as by stimulating at least the fornix. System 10 can be constructed and arranged to increase or maintain (e.g. prevent the decrease of) one or more portions of hippocampal volume, such as by stimulating the fornix. Fornix or other brain tissue stimulation with the systems and devices of the present inventive concepts can increase local blood flow and perfusion of the hippocampus, increase angiogenesis and/or promote trophic release of endothelial growth factor, BDNF and/or other neuroprotective agents (e.g. to increase or maintain one or more portions of hippocampal volume). In some embodiments, the stimulation of system 10 results in neurogenesis, such as hippocampal neurogenesis.

System 10 can be constructed and arranged to produce clinical benefits to the patient by modulating neurophysiologic activity in pathological circuits. The pathological circuits can be causing functional impairment in the neural elements and circuits underlying cognitive and/or memory functions, and the stimulation provided by system 10 can improve clinical and/or neurobiological outcomes that result from these pathological circuits. Stimulation provided by system 10 can be used to modulate dysfunctional networks, such as to therapeutically manipulate the levels of one or more deleterious proteins.

System 10 can be constructed and arranged to drive activity in projection structures downstream from the stimulation site (e.g. downstream from the fornix). System 10 can be constructed and arranged to provide evoked responses that are unequivocal and/or consistent. Stimulation delivered by system 10 can activate the cingulated gyrus and precuneus area of the parietal lobe, including direct and trans-synaptic sequential activation of downstream targets related to the connectivity of the fornix and hippocampus.

System 10 can be constructed and arranged to regulate the level of one or more neurotrophic factors and/or neurotransmitters. System 10 can be constructed and arranged to ameliorate cognitive decline associated with dementia. A patient receiving therapy from system 10 can have reduced integrity of white matter tracts innervating limbic structures such as the fornix (e.g. at least the fornix), such as can be determined by fractional anisotropy maps using diffusion tensor imaging. System 10 can be constructed and arranged to achieve at least one of: treats memory impairment; improves memory function; treats cognitive function loss; reverses synaptic loss; improves cognitive function; reduces degradation of cognitive function; promotes neurogenesis in the hippocampus of patient's brain B; drives neurotrophin expression; regulates one or more biomarkers related to Alzheimer's Disease such as amyloid-beta, tau, and/or phosphorylated tau; regulates BDNF expression; increases neurotransmitter release such as acetylcholine; or improves glucose utilization in the temporal lobe, the parietal lobe or both lobes of the patient's brain B.

In some embodiments, a combination of treatment therapies can be delivered to provide influencing of multiple neuronal types. Stimulator 100 can be constructed and arranged to deliver multiple therapies, such as two or more stimulation therapies selected from the group consisting of: electrical stimulation; magnetic stimulation; optical stimulation (e.g. visible, ultraviolet and/or infrared light); sound stimulation (e.g. ultrasound or subsonic waves); chemical stimulation (e.g. a drug or other agent); and combinations of these, such as are described hereinabove. For example, it can be desirable to concurrently influence, via chemical, electrical and/or other stimulation, the neurons in the fornix, hippocampus and/or other portions of brain B to achieve an improved result. A system 10 utilizing multiple forms of treatment therapy can be similar to that which is disclosed, for example, in U.S. Pat. No. 5,782,798. In addition to affecting the deep brain, it can be desirable for system 10 to affect concurrently other portions of the brain.

In some embodiments, system 10 is constructed and arranged to provide one or more pharmaceutical or other agents, such as an agent delivered orally, via an injection, or delivered by a component of system 10. In some embodiments, system 10 is constructed and arranged to provide a cholinesterase inhibitor medication or other agent to the patient. Stimulation element 150 can be constructed and arranged to deliver one or more pharmaceutical or other agents, such as when stimulation element 150 is at least configured as a drug delivery element or other liquid or solid dispensing element.

As described above, controller 200 is constructed and arranged to set one or more stimulation parameters 105 of system 10, such as an initial setting of one or more stimulation parameters 105 (e.g. to cause an initial treatment stimulation energy to be delivered to brain B) or a modification to an existing set of one or more stimulation parameters 105 (e.g. to modify the treatment stimulation energy being delivered to brain B). Initial settings of stimulation parameters 105 and/or modifications to existing settings can be made to provide sufficient therapy (e.g. cause a desired event) and/or to reduce the likelihood or effect of one or more adverse events. Setting of one or more stimulation parameters 105 can be made by an operator of system 10 using controller 200, such as an operator who is a clinician or other caregiver of the patient. Alternatively or additionally, setting of one or more stimulation parameters 105 can be performed automatically or semi-automatically by system 10, such as in a closed loop fashion based on information received from diagnostic tool 300 or another component of system 10.

Controllers 200a and 200b comprise user interfaces 201a and 201b, respectively (singly or collectively user interface 201). User interface 201 can comprise one or more user input or user output components, such as a component selected from the group consisting of: switch; membrane switch; mouse; keyboard; microphone; a graphical and/or alphanumeric screen; touch screen; light; speaker or other audio transducer; vibrational or other tactile transducer; and combinations of these. User interface 201 can be configured to provide information to and/or receive commands from an operator of system 10 (e.g. the patient, a family member of the patient, and/or a clinician or other healthcare provider). Controller 200 can comprise one or more handheld devices configured to program or otherwise communicate with stimulator 100 and/or diagnostic tool 300. Pathway 20 can comprise a uni-directional or bi-directional communication pathway between controller 200 and stimulator 100. Pathway 20 can comprise one or more physical conduits such as electrically conductive wires and/or optical fibers. Alternatively or additionally, pathway 20 can comprise a wireless communication pathway, such as a transmission of electromagnetic waves such as is used in wireless radiofrequency (RF) communications.

Diagnostic tool 300 can be constructed and arranged to record, gather, assess, collect, determine and/or otherwise measure one or more patient parameters and produce diagnostic data 305 representing these one or more patient parameters. Diagnostic tool 300 can be further constructed and arranged to process (e.g. mathematically process) and/or combine measured data, such as when diagnostic tool 300 comprises one or more algorithms configured to analyze diagnostic data 305, such as one or more algorithms that compare diagnostic data 305 to one or more "stimulation thresholds" (as described hereinbelow) and record one or more stimulation parameters associated with the one or more stimulation thresholds. In some embodiments, an algorithm is constructed and arranged to determine a stimulation threshold correlating to an undesired clinical event or other undesired patient event (hereinafter "adverse event") as described herein. In some embodiments, an algorithm is constructed and arranged to determine a stimulation threshold correlating to a desired clinical event or other desired patent event (hereinafter "desired event"), such as an event in which a desired memory recall occurs, a desired memory learning is achieved and/or other desired event as described hereinbelow.

System 10 (e.g. automatically or semi-automatically) and/or an operator of system 10 can use the diagnostic data 305 to set and/or modify the stimulation provided by stimulator 100. Setting of one or more stimulation parameters 105 using or otherwise based on diagnostic data 305 can be performed to improve the therapy achieved by system 10. Alternatively or additionally, setting of one or more stimulation parameters 105 based on diagnostic data 305 can be performed to at least one of reduce and/or prevent (hereinafter "reduce") an adverse event for the patient. Diagnostic data 305 can be used to determine if an adverse event has occurred or is about to occur. Alternatively or additionally, diagnostic data 305 can be used to determine if a desired event has occurred or is about to occur. In each of these instances, the particular stimulation parameters 105 causing the adverse event or desired event represent a stimulation threshold for that particular event.

In some embodiments, a stimulation parameter 105 is set at a level below or otherwise away from (hereinafter "below") the stimulation threshold that caused an adverse event (e.g. as determined in a diagnostic test of the present inventive concepts). In these embodiments, the term "below" does not necessarily correlate to a lower magnitude of stimulation energy, but represents a lower, greater or different value that tends toward avoiding occurrence of the adverse event. For example, if flow rates of 5 ml/hr or less of an agent infused by stimulation element 150 caused an adverse event, stimulation parameter 105 could be set to a level of more than 5 ml/hr to avoid the adverse event. In some embodiments, a stimulation parameter 105 is set at a safety margin below the stimulation threshold (e.g. a voltage or current level that is less than the level causing the adverse event). In some embodiments, an approximate 50% safety margin is used (e.g. a voltage or current is set to approximately half the voltage or current causing the adverse event). In other embodiments, a safety margin of at least 10% is used, such as a safety margin of at least 20%, 30%, 40% or 50%.

In some embodiments, a treatment stimulation parameter $105_{Treat}$ is set to a level at or above (hereinafter "above") a stimulation threshold that caused a desired event (e.g. as determined in a diagnostic test of the present inventive concepts). In these embodiments, the term "above" does not necessarily correlate to a higher magnitude of stimulation energy, but represents a higher, lower or similar value that tends toward causing occurrence of the desired event.

Diagnostic tool 300 can comprise a user interface 301, such as a user interface configured to provide information to and receive commands from an operator of system 10. User interface 301 can comprise one or more user input and/or user output components selected from the group consisting of: a touchscreen; a graphical and/or alphanumeric screen; a keypad; a mouse; and combinations thereof. As described above, diagnostic tool 300 is constructed and arranged to measure one or more patient parameters and produce diagnostic data 305 which is determined based on the one or more measured patient parameters. Diagnostic data 305 can be displayed on user interface 301 (such as heart rate information, blood pressure information, or other data corresponding to a measured patient parameter that is displayed on user interface 301). In some embodiments, diagnostic tool 300 can communicate directly with controller 200 and/or stimulator 100, such as via a wired or wireless connection as described herein, such that diagnostic data 305 is recorded by controller 200 and/or stimulator 100, such as to automatically and/or semi-automatically modify one or more stimulation parameters 105.

As described herein, diagnostic data 305 can be used to determine if an adverse event has occurred or is about to occur. Treatment stimulation parameters $105_{Treat}$ can be set at a level below or otherwise different than the stimulation threshold at which the adverse event occurred, such as at a safety margin below or otherwise away from that stimulation threshold (e.g. a voltage or current level that is less than the level causing the adverse event). In some embodiments, one or more treatment stimulation parameters $105_{Treat}$ are modified based on a stimulation threshold (e.g. modified to a level at or below the stimulation threshold, such as at a safety margin below the stimulation threshold at which an adverse event occurred). For example, an adverse event that occurs at a signal voltage of 6 Volts, may result in delivering therapy at 5 Volts (a 16.6% safety margin), at 4 Volts (a 33.3% safety margin) or at 3 Volts (a 50% safety margin).

Diagnostic tool 300 can comprise one or more diagnostic devices, such as one or more devices selected from the group consisting of: heart rate monitor; EKG measurement device; oximeter; combined heart rate and oximeter device such as a pulse oximeter; blood pressure measurement device; neuronal activity measurement device; EEG measurement device; sleep measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations of these. Diagnostic tool 300 can be constructed and arranged to detect and/or record an adverse event, such as an adverse event selected from the group consisting of: undesirable heart rate; undesirable respiration rate; undesirable sweating; undesirable hallucinations; undesirable tingling; flushing; undesirable psychiatric effect; undesirable cognitive effect; unpleasant generalized warming; undesirable perceptions described as déjà vu; seizure; synchronized neuronal firing pattern; undesired neural response time; undesired brain state; undesired theta phase; undesired p300 amplitude; and combinations of these.

In some embodiments, diagnostic tool 300 comprises two independent diagnostic measurement devices, for example two devices whose diagnostic data are used in combination. For example, diagnostic tool 300 can comprise a blood pressure measurement device and a heart rate measurement device, such as to identify patient discomfort or other patient issue (e.g. a falsehood or other inaccurate statement made by the patient that can be detected through analysis of a patient parameter such as heart rate and/or blood pressure).

Diagnostic tool 300 can comprise a memory test such as a verbal, visual, motor function and/or spatial memory test. Diagnostic tool 300 can be constructed and arranged to detect and/or record a memory recall event, such as a tool including an EEG measurement device (e.g. an EEG device configured to detect one or more brain states of the patient and/or a form configured to manually record the results of a memory test.

In embodiments where diagnostic tool 300 comprises an EKG measurement device, one or more treatment parameters $105_{Treat}$ can be set based on a stimulation threshold at which undesired EKG activity is identified in diagnostic data 305.

In embodiments where diagnostic tool 300 comprises a neuronal activity measurement device, diagnostic tool 300 can be constructed and arranged to measure a neuronal parameter selected from the group consisting of: single neuron activity; local field potential; event related potential; electroencephalogram reading; electrocorticogram reading; and combinations of these. In these embodiments, a stimulation threshold (e.g. a stimulation threshold at which an adverse event is recorded by diagnostic tool 300) can be determined when an adverse event occurs that is selected from the group consisting of: seizure; synchronized neuronal firing pattern; undesired neural response time; undesired brain state; undesired theta phase; undesired p300 amplitude; and combinations of these.

In embodiments where diagnostic tool 300 comprises an ERP measurement device, one or more treatment parameters $105_{Treat}$ can be set based on a stimulation threshold at which undesired EPR activity is identified in diagnostic data 305.

In embodiments where diagnostic tool 300 comprises a blood pressure measurement device, one or more treatment parameters $105_{Treat}$ can be set based on a stimulation threshold at which undesired blood pressure readings are identified in diagnostic data 305. In these embodiments, diagnostic tool 300 can further comprise a heart rate measurement device, such that diagnostic data comprises both blood pressure readings and heart rate readings.

In embodiments where diagnostic tool 300 comprises a blood oxygen measurement device, one or more treatment parameters $105_{Treat}$ can be set based on a stimulation threshold at which undesired blood oxygen readings are identified in diagnostic data 305.

In embodiments where diagnostic tool 300 comprises a body motion measurement device, one or more treatment parameters $105_{Treat}$ can be set based on a stimulation threshold at which undesired body motion (e.g. a tremor) is identified in diagnostic data 305.

In embodiments where diagnostic tool 300 comprises a neurochemical analysis device, the neurochemical analysis device can be constructed and arranged to measure a parameter selected from the group consisting of: neurotransmitter level (GABA, glutamate, acetylcholine, dopamine, epinephrine, etc.); a pH concentration; an ion concentration; a lactate level; cerebral blood flow; glucose utilization; oxygen extraction; and combinations of these. One or more treatment parameters $105_{Treat}$ can be set based on a stimulation threshold at which undesired neurochemical activity and/or level is identified in diagnostic data 305.

In embodiments where diagnostic tool 300 comprises an imaging device, one or more treatment parameters $105_{Treat}$ can be set based on a stimulation threshold at which an undesired patient image is identified in diagnostic data 305. Diagnostic tool 300 can comprise an imaging device selected from the group consisting of: MRI; fMRI; X-ray; fluoroscope; Ct-Scanner; PET Scanner; Diffusion Tensor Imaging (DTI) device; ultrasound imaging device; standardized Low Resolution Brain Electromagnetic Tomography (sLORETA) device; MagnetoEncephalography (MEG); and combinations of these, such as when used to produce diagnostic data 305 that quantifies or qualifies the effects of receiving stimulation from system 10 and/or when used to position stimulation element 150. In these embodiments, an image produced by diagnostic tool 300 can be used to optimize therapy or reduce an adverse event, such as when used to select an electrode to receive stimulation energy based on its position relative to a target as described herein. An image produced by diagnostic tool 300 can be used to select one or more stimulating elements from a set of multiple stimulating elements (e.g. to select one or more electrodes from a set of multiple electrodes based on an image of the multiple electrodes in reference to a target stimulation location such as the fornix).

In some embodiments, diagnostic tool 300 produces data to assess axonal pathways, such as an assessment performed during stimulation of the axonal pathways or locations proximate the assessed pathways. In these embodiments, diagnostic data 305 produced by diagnostic tool 300 can be used to identify one or more axonal pathways that may be necessary or at least desirable to optimize therapeutic benefit from the stimulation provided by system 10. Diagnostic tool 300 can comprise at least a diffusion tensor imaging (DTI) device and/or a tractography-activation model (TAM) used to identify the pathways stimulated by system 10. The TAM can consist of: anatomical and diffusion-weighted imaging data acquired on the patient; probabilistic tractography from the brain region surrounding one or more stimulation elements; finite element models of the electric field generated by stimulator 100; and/or application of the electric field produced by one or more stimulation elements 150 to multi-compartment cable models of axons, with trajectories defined by the tractography, to predict action potential generation in the pathways. Diagnostic tool 300 can be configured to produce clinical data, diffusion tensor tractography, and/or computer models of tissue-specific stimulation areas, such as to determine one or more axonal pathways being stimulated and/or to predict or differentiate the therapeutic benefit of their stimulation.

Diagnostic tool 300 can comprise a patient assessment recording tool, such as a tool selected from the group consisting of: a form; an electronic form; a tablet; a personal computer; a database; and combinations of these. In these embodiments, the patient assessment can comprise an assessment selected from the group consisting of: an assessment received verbally from the patient; an assessment received in written form from the patient; an assessment made by a caregiver of the patient; and combinations of these. The patient assessment can comprise an assessment of a patient state selected from the group consisting of: depression; paranoia; schizophrenia; suicidality; suicide ideation; apathy; anxiety; mania; and combinations of these. Diagnostic tool 300 can comprise an algorithm configured to analyze data on a patient assessment form or other patient assessment tool.

In some embodiments, diagnostic tool 300 comprises one or more sensors 330 as shown. One or more sensors of system 10, such as sensor 330, sensor 230a, 230b and/or sensor 109 can comprise a sensing element selected from the group consisting of: neuronal activity sensor; EEG sensor; polysomnography (PSG) sensor; sleep sensor; sleep state sensor; local field potential sensor; neurochemical sensor; pH sensor; pressure sensor; blood pressure sensor; optical sensor; blood gas sensor; blood oxygen sensor; magnetic sensor; strain gauge; temperature sensor; and combinations of these. Sensor 330, sensor 230a, 230b and/or sensor 109 can comprise an implanted or external sensor. Stimulating element 150 can comprise sensor 330. Sensor 330, sensor 230a, 230b and/or sensor 109 can comprise at least one electrode. System 10 can be constructed and arranged to provide closed loop stimulation based on one or more signals received from one or more of sensors 330, 230a, 230b and/or 109.

As described hereinabove, one or more portions of stimulator 100 can be implanted in the patient, such an implantation of stimulation element 150. Diagnostic tool 300 can be constructed and arranged to gather diagnostic data 305 before and/or after implantation of stimulation element 150. In some embodiments, diagnostic tool 300 gathers diagnostic data 305 to determine a stimulation threshold at least 5 minutes after implantation of stimulation element 150. In some embodiments, diagnostic tool 300 gathers diagnostic data 305 to determine a stimulation threshold at least 24 hours after implantation of stimulation element 150, or at least 2 weeks after implantation of stimulation element 150.

As described above, controller 200 and stimulator 100 can be constructed and arranged to stimulate brain B with one or more temporary or test stimulation parameters $105_{Test}$. Diagnostic tool 300 can be constructed and arranged to measure one or more patient parameters while brain B is being stimulated with these test stimulation parameters $105_{Test}$, producing diagnostic data 305 correlating to the test stimulation parameters $105_{Test}$. In some embodiments, multiple sets of similar or dissimilar test stimulation parameters $105_{Test}$ are delivered to brain B, while diagnostic tool 300 measures at least one patient parameter and produces diagnostic data 305. In some embodiments, a series of varied test stimulation parameters $105_{Test}$ can be delivered to brain B (e.g. a stepped or continuous increase in stimulation energy level, such as a stepped or continuous increase of a stimulating voltage and/or current), while diagnostic tool 300 measures at least one patient parameter and produces a set of diagnostic data 305 which is correlated to the particular level of test stimulation parameters $105_{Test}$ associated with each subset of diagnostic data 305. Subsequently, stimulator 100 delivers treatment stimulation energy comprising one or more treatment stimulation parameters $105_{Treat}$ that are based on the produced diagnostic data 305. In some embodiments, one or more treatment stimulation parameters $105_{Treat}$ are programmed into stimulator 100 via controller 200. In some embodiments, system 10 is constructed and arranged to automatically set one or more treatment stimulation parameters $105_{Treat}$ based on the produced diagnostic data 305.

In some embodiments, diagnostic data 305 produced by diagnostic tool 300 is used to determine an initial (e.g. first time) set of treatment stimulation parameters $105_{Treat}$. In some embodiments, diagnostic data 305 produced by diagnostic tool 300 is used to modify a pre-existing set of treatment stimulation parameters $105_{Treat}$. In some embodiments, diagnostic data 305 produced by diagnostic tool 300 is used to determine test stimulation parameters $105_{Test}$, such as diagnostic data 305 collected in a previous test. In these embodiments, a test stimulation parameter $105_{Test}$ can be set based on a stimulation threshold at which an adverse event is detected by diagnostic tool 300.

In some embodiments, stimulator 100 stimulates brain B with a first set of test stimulation parameters $105_{Test}'$ for a first time period and a second set of test stimulation parameters $105_{Test}''$ for a second time period. The first time period and the second time period can comprise relatively the same length of time or different lengths of time. The first and/or second time period can comprise a time period less than or equal to 24 hours, such as less than or equal to 6 hours, 3 hours, 1 hour, 30 minutes, 15 minutes, 10 minutes, 5 minutes or 2 minutes. Diagnostic tool 300 measures at least one patient parameter during all or a portion of both the first time period and the second time period, and produces first diagnostic data 305' and second diagnostic data 305", representing the measured at least one patient parameter recorded during the first time period and the second time period, respectively. Subsequently, stimulator 100 provides stimulation energy to brain B comprising one or more treatment stimulation parameters $105_{Treat}$ that are determined based on the first diagnostic data 305' and second diagnostic data 305". In these embodiments, treatment stimulation parameters $105_{Treat}$ can be based on one or more test stimulation parameters $105_{Test}$ associated with a desired treatment and/or they can be based on one or more test stimulation parameters $105_{Test}$ associated with avoiding an adverse event, such as described herein.

In some embodiments, the treatment stimulation parameters $105_{Treat}$ equal or at least approximate the first set of test stimulation parameters $105_{Test}'$ or the second set of test stimulation parameters $105_{Test}''$. The treatment stimulation parameters $105_{Treat}$ chosen can approximate a test stimulation parameter $105_{Test}$ associated with an improved or otherwise desired treatment of a neurological disease and/or disorder. The improved treatment can correspond with a therapeutic benefit such as a desired memory recall with the patient. Alternatively or additionally, the treatment stimulation parameters $105_{Treat}$ chosen can approximate a test stimulation parameter $105_{Test}$ associated with avoidance of an adverse event. In some embodiments, the treatment stimulation parameters $105_{Treat}$ chosen can be proportional or otherwise based on a test stimulation parameter $105_{Test}$ associated with avoidance of an adverse event as described hereinabove, such as when treatment stimulation parameters $105_{Treat}$ are a safety margin below the test stimulation parameters $105_{Test}$ at which the adverse event occurred, as described herein.

In some embodiments, one or more treatment stimulation parameters $105_{Treat}$ are programmed into stimulator 100 via controller 200. Alternatively, system 10 is constructed and arranged to automatically set one or more treatment stimulation parameters $105_{Treat}$ based on the produced diagnostic data 305.

Diagnostic tool 300 used in the first time period and the second time period can comprise one or more diagnostic devices or other tools, such as are described herein and producing diagnostic data 305. In some embodiments, diagnostic data 305 produced by a diagnostic tool 300 is used to determine first test stimulation parameters $105_{Test}'$ and/or second test stimulation parameters $105_{Test}''$, such as diagnostic data 305 collected in a previous test performed using diagnostic tool 300. In some embodiments, diagnostic tool 300 comprises a memory test tool, such as a form used to record memory data. In these embodiments, treatment stimulation parameters $105_{Treat}$ can approximate or otherwise be based on the test stimulation parameters $105_{Test}$ that resulted in a higher memory test score recorded in one of a set of time periods (e.g. two or more time periods) between which one or more test stimulation parameters were varied.

One or more treatment stimulation parameters $105_{Treat}$ can comprise an electrical stimulation parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; and combinations of these. In some embodiments, stimulation element 150 comprises a brain inserted lead comprising multiple electrodes, and a treatment stimulation parameter $105_{Treat}$ or other stimulation parameter 105 can represent a selection (e.g. a subset) of the electrodes that receive stimulation energy. The selection of electrodes can comprise a single electrode, a pair of electrodes, or more than two electrodes, such as one or more electrodes that receive monopolar or bipolar energy. In some embodiments, a stimulation parameter 105 comprises a signal voltage of between 0.1 Volts and 10.0 Volts, such as a voltage between 1.0 Volts and 6.0 Volts, or between 1.0 Volts and 3.0 Volts. In some embodiments, a stimulation parameter 105 comprises a voltage less than or equal to 9.0 Volts, such as less than or equal to 8.0 Volts, 7.0 Volts, 6.0 Volts, 5.0 Volts, 4.0 Volts or 3.5 Volts. In some embodiments, a stimulation parameter 105 comprises a signal frequency between 2 Hz and 1000 Hz, such as a frequency of approximately 130 Hz. Energy delivery can be given in a series of on and off times, such as when a stimulation parameter 105 comprises an on-time of approximately 30 µseconds to 200 µseconds, such as with an on time of 90 µseconds. A stimulation parameter 105 can comprise a parameter associated with duration of energy delivery, such as a parameter corresponding to continuous delivery of energy (e.g. continuous delivery of pulsed energy) or a parameter corresponding to intermittent energy delivery comprising one or more energy delivery periods ranging from thirty minutes to 24 hours.

In some embodiments, a stimulation parameter 105 comprises a light stimulation parameter selected from the group consisting of: power of light delivered to tissue; frequency of light delivered to tissue; modulation parameter of light delivered to tissue; and combinations of these.

In some embodiments, a stimulation parameter 105 comprises a sound stimulation parameter selected from the group consisting of: amplitude of sound delivered to tissue; frequency of sound delivered to tissue; modulation parameter of sound delivered to tissue; and combinations of these.

In some embodiments, a stimulation parameter 105 comprises an agent delivery stimulation parameter selected from the group consisting of: mass of agent delivered to tissue; volume of agent delivered to tissue; concentration of agent delivered to tissue; delivery rate of agent delivered to tissue; and combinations of these.

In some embodiments, controller 200 and/or another component of system 10 are constructed and arranged to set at least one treatment stimulation parameter $105_{Treat}$ based on a stimulation threshold at which an adverse event is detected by diagnostic tool 300, such as an adverse event as described hereinabove. In these embodiments, the at least one treatment stimulation parameter $105_{Treat}$ can be set to a level at or below the stimulation threshold, such as at a safety margin below the stimulation threshold as described hereinabove.

In some embodiments, controller 200 and/or another component of system 10 are constructed and arranged to set at least one treatment stimulation parameter $105_{Treat}$ based on a stimulation threshold at which a desired event is detected by diagnostic tool 300. Patient desired events include events selected from the group consisting of: recall of a desired memory; achievement of desired memory learning; desired level of neuronal activity; acceptable physiologic condition such as an acceptable heart rate or acceptable level of neuronal activity; experiential phenomena such as those described in epilepsy literature; and combinations of these. In these embodiments, the at least one treatment stimulation parameter $105_{Treat}$ can be set to a level at or above the stimulation threshold, such as at a pre-determined percentage above the stimulation threshold. In these embodiments, the at least one treatment stimulation parameter $105_{Treat}$ can also be set based on a second stimulation threshold at which an adverse event occurred, such as a safety margin below the adverse event stimulation threshold. For example, a memory recall event may be recorded by diagnostic tool 300 at a stimulation voltage of X Volts, and an adverse event may be recorded by diagnostic tool 300 at a stimulation voltage of Y Volts, where Y is greater than X. A treatment stimulation parameter $105_{Treat}$ can be set to a signal voltage between X Volts and Y Volts.

System 10 can be constructed and arranged to provide open loop stimulation to brain B. Alternatively or additionally, system 10 can be constructed and arranged to provide closed loop stimulation to brain B, such as closed loop stimulation based on diagnostic data 305 provided by diagnostic tool 300 and/or a signal provided by one or more of sensors 309, 109 and 209, or a separate implanted or external sensor, such as sensor 109 described in reference to FIG. 3 hereinbelow.

In some embodiments, diagnostic tool 300 and/or another component of system 10 comprises data logging assembly 350. Data logging assembly 350 can be constructed and arranged to record one or more events that occur during delivery of test stimulation energy using test stimulation parameters $105_{Test}$, such as when stimulation energy is varied. Data logging assembly 350 can be configured to record diagnostic data 305, such as to determine a minimum, maximum, average and/or other statistical value of diagnostic data 305 (e.g. a maximum heart rate or a maximum blood pressure that occurs during delivery of test stimulation energy). In some embodiments, data logging assembly 350 comprises an assembly with a button that a patient can activate (e.g. press), such as during a patient adverse event or a memory recall event as noticed by the patient. In some embodiments, at least a portion of data logging assembly 350 can be at a location remote from the patient, such as at one or more file locations accessible via the Internet or other information access network. Diagnostic data 305 from multiple patients could be stored in one or more locations remote from those patients. Diagnostic data 305 recorded by one or more diagnostic tools 300 during diagnostic tests performed on one or more patients can be processed, analyzed and/or otherwise used to determine one or more treatment stimulation parameters $105_{Treat}$ for one or more patients.

Figure 2:
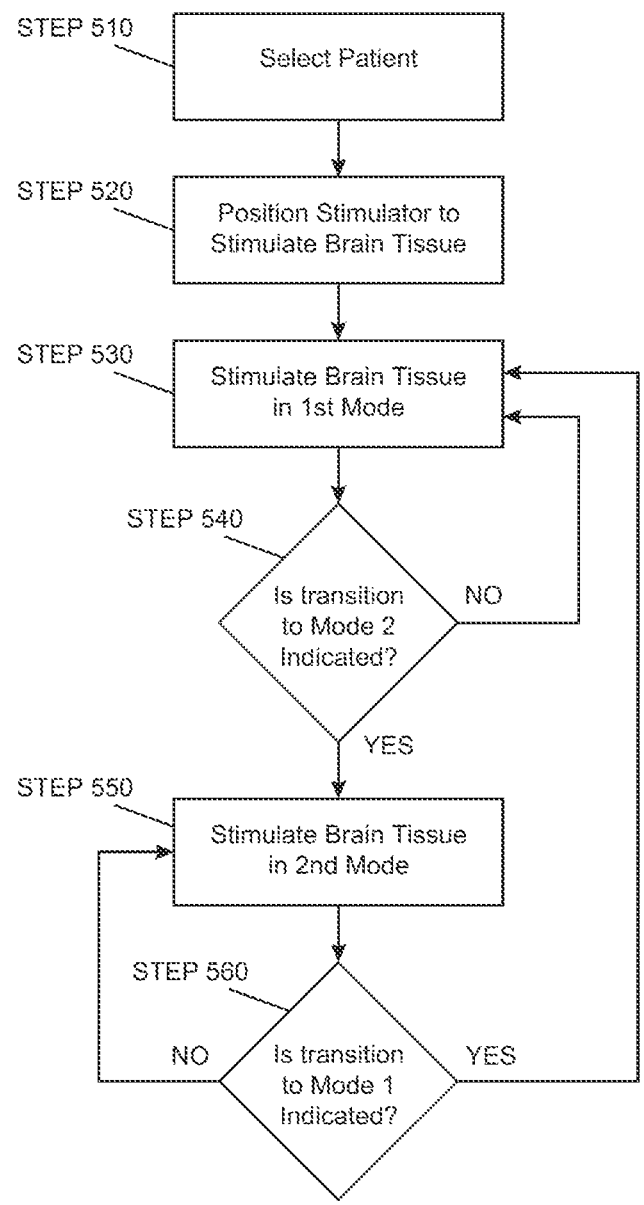
FIG. 2 illustrates a flow chart of a method for treating a patient with a brain stimulation system, consistent with the present inventive concepts.

Referring now to FIG. 2 a flow chart of a series of steps for treating a patient with a stimulation system is illustrated, consistent with the present inventive concepts. The method comprises STEPs 510 through 550, which can be performed using one or more components of system 10 of FIG. 1 described hereinabove. In STEP 510, a patient is selected for implantation. In a preferred method, the patient is screened for candidacy as described in reference applicants co-pending U.S. patent application Ser. No. 13/655,652, entitled "Deep Brain Stimulation of Memory Circuits in Alzheimer's Disease", filed Oct. 19, 2012, the content of which is incorporated herein by reference in its entirety. In some embodiments, the selected patient is a patient diagnosed and/or prognoses with a cognitive disorder selected from the group consisting of: Alzheimer's Disease (AD) such as Mild or Moderate Alzheimer's Disease; probably Alzheimer's Disease; a genetic form of Alzheimer's Disease; Mild Cognitive Impairment (MCI); hippocampal damage such as hippocampal damage due to Alzheimer's disease, anoxia, epilepsy or depression; neuronal loss; neuronal damage; chemotherapy induced memory impairment; epilepsy; a seizure disorder; dementia; amnesia; a memory disorder such a spatial memory disorder; cognitive impairment associated with Schizophrenia; Parkinson's Disease related cognitive impairment or dementia; post-traumatic stress disorder (PTSD); traumatic brain injury (TBI); and combinations of these. Additionally or alternatively, the patient can be selected to treat negative symptoms of a disease or disorder selected from the group consisting of: schizophrenia; depression; post-traumatic stress disorder (PTSD); traumatic brain injury (TBI); other conditions of reversible impaired memory or cognition; and combinations of these.

In STEP 510, or in another step of the method of FIG. 2, at least one imaging procedure can be performed on the patient, collecting at least one patient image. In a preferred embodiment, the imaging procedure is an MRI procedure performed to identify the fornix of the patient and/or one or more other brain locations. Alternatively or additionally, different patient imaging procedures can be used including imaging procedures selected from the group consisting of: X-ray; ultrasound imaging; fMRI; PET scan; and combinations of these. Multiple imaging procedures can be performed, such as similar imaging procedures performed at different times, or different imaging procedures performed at the same or different times. In one embodiment, a first imaging procedure is performed at least 7 days prior to a second imaging procedure. In another preferred embodiment, a first imaging procedure is an MRI procedure and a second imaging procedure is selected from the group consisting of: a second MRI procedure; an X-ray; an ultrasound imaging procedure; an fMRI; a PET scan; and combinations of these. Multiple patient images, collected in one or more similar or dissimilar imaging procedures, can be collected. These images can be used in combination, in comparison, or both. In some embodiments, the two procedures are performed at different times and one or more patient parameters are compared, such as parameters selected from the group consisting of: brain size; brain shape; and brain thickness. In some embodiments, an amyloid PET scan can be used to assess the presence of amyloid in a patient. In some embodiments, a resting state BOLD fMRI sequence is performed to evaluate Default Mode Network or other brain state. In some embodiments, Diffusion Tensor Imaging and tractography is performed, such as to create an image of microstructures of the brain to assess white matter abnormalities (e.g. of the fornix).

In STEP 520, a stimulator is positioned to stimulate at least a portion of the patient's brain. In some embodiments, at least a portion of a brain stimulator is implanted, such as an implantation of one or more portions of stimulator 100 described in reference to FIG. 1 hereinabove and/or stimulator 100 described in reference to FIG. 3 hereinbelow. In some embodiments, one or more leads (e.g. multiple electrode leads) are positioned as described in applicant's co-pending International PCT Patent Application Serial Number PCT/CA2015/050249, titled "Systems and Methods for Determining a Trajectory for a Brain Stimulation Lead", filed Mar. 31, 2015; the content of which is incorporated herein by reference in its entirety.

The one or more implantable portions of stimulator 100 can be implanted in one or more surgeries. The surgery can include implantation of a lead comprising one or more electrodes, such as one or more electrodes positioned proximate the fornix of the patient's brain B. One or more stimulating elements such as electrodes can be implanted in a location selected from the group consisting of: in the Papez Circuit of the patient's brain; approximately 2 mm anterior and parallel to the vertical portion of the fornix; in the optic tract such that the ventral most contact is 2 mm above the dorsal surface of the optic tract; approximately 5 mm from the midline; and combinations of these. A post-operative imaging procedure such as an MRI can be performed to assess and/or confirm position of one or more implanted electrodes or other components of the system, such as to confirm location of multiple electrodes relative to the fornix or other target location within the patient's brain. One or more diagnostic tools, such as diagnostic tool 300 described hereinabove in reference to FIG. 1, can be used to gather diagnostic data used to position the stimulator. The diagnostic tool can be an imaging device, and the diagnostic data can include one or more images produced by the diagnostic device used to select one or more electrodes or other stimulating elements configured to receive stimulation energy. The one or more stimulating elements can be selected based on their proximity and/or relative position to a stimulation target, such as the fornix. For example a first electrode providing stimulating energy generating a first set of diagnostic data can be selected over a second electrode providing stimulating energy and generating a second set of similar diagnostic data (e.g. similar therapeutic benefit) based on information provided by an imaging device (e.g. when the first electrode is in a more desirable position relative to a stimulation target than the second electrode). In some embodiments, electrode selection is made based on image data to prevent stimulation on non-target tissue.

In alternative embodiments, brain stimulation is provided by an external, non-invasive stimulation device (i.e. one or more fully non-implanted stimulation system components). In embodiments including an implanted stimulator or a portion of a stimulator that is implanted, at least one stimulation element can be implanted in, on or near the brain of a patient. The at least one stimulation element can be positioned in, on or near the brain of the patient based on the at least one patient image. The at least one stimulation element can be placed via a visual analysis of the at least one image, and/or one or more mathematical or other computational analysis or analyses of the patient image. In some embodiments, the at least one stimulation element is positioned in or around the fornix of the patient's brain, as has been described in hereinabove. In another embodiment, the at least one stimulation element, such as a stimulation element comprising at least two electrodes, is positioned to provide bipolar stimulation of the fornix or other brain tissue. The at least one stimulation element can comprise at least one electrode configured to deliver electrical energy. Proper positioning of the stimulation element can be confirmed after placement, such as with a subsequent MRI image.

The stimulation element, such as one or more stimulation elements 150 of stimulator 100 of FIG. 1, can comprise an electrical stimulation element such as an electrode or a magnet such as an electromagnet. Alternatively or additionally, the stimulation element can comprise an optical stimulation element, such as a visible light element; an infrared light element; and combinations of these. Alternatively or additionally, the stimulation element can comprise a chemical stimulation element, such as a drug or other agent delivery assembly. The drug delivery assembly can be configured to deliver one or more of: biologically active molecules; neurotransmitters; and neurotrophic factors. The stimulation element can deliver one or more drugs or pharmaceutical agents, and delivery rate or drug concentration can be determined based on patient tolerance, such as a tolerance determined in a titration procedure performed using diagnostic tool 300 of FIG. 1. In a particular embodiment, the stimulation element is constructed and arranged to deliver a cholinesterase inhibitor. In another particular embodiment, an electrode and a second stimulation element is included. The second stimulation element can comprise an element selected from the group consisting of: a second electrode; a magnet; an optical element; a chemical or other agent delivery assembly; and combinations of these.

In STEP 530, at least a portion of a patient's brain is stimulated in a first mode using a first set of stimulation parameters, such as stimulation parameters 105*a* described hereinabove in reference to FIG. 1.

In STEP 540, a check is performed, such as via algorithm 106 of stimulator 100 described hereinabove in reference to FIG. 1, to determine if stimulator 100 should transition to a second mode of stimulation. If the transition is not indicated, STEP 530 is repeated in which stimulation remains in the first mode of stimulation and a subsequent check is performed in a subsequent performance of STEP 540. If the transition is indicated, STEP 550 is performed.

In STEP 550, at least a portion of a patient's brain is stimulated in a second mode using a second set of stimulation parameters, such as stimulation parameters 105*b* described hereinabove in reference to FIG. 1. In some embodiments, the second set of stimulation parameters 105*b* correlate to at least a different portion of the patient's brain being stimulated that was not stimulated in the first mode of stimulation. In some embodiments, the second set of stimulation parameters 105b correlate to at least a portion of the patient's brain being stimulated in the first mode, not being stimulated in the second mode. Alternatively or additionally, the first set of stimulation parameters 105a and the second set of stimulation parameters 105b differ in the type and/or amount of stimulation delivered to similar or dissimilar portions of the patient's brain, such as different stimulation parameters correlating to a parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; agent delivery rate; physiologic concentration; power of light delivered to tissue; frequency of light delivered to tissue; a modulation parameter of light delivered to tissue; amplitude of sound delivered to tissue; frequency of sound delivered to tissue; a modulation parameter of sound delivered to tissue; mass of agent delivered to tissue; volume of agent delivered to tissue; concentration of agent delivered to tissue; delivery rate of agent delivered to tissue; and combinations of these.

In STEP 560, a check is performed, such as via algorithm 106 of stimulator 100 described hereinabove in reference to FIG. 1, to determine if stimulator 100 should transition from the second mode of stimulation to the first mode of stimulation. If the transition is not indicated, STEP 550 is repeated in which stimulation remains in the second mode of stimulation and a subsequent check is performed in a subsequent performance of STEP 560. If the transition is indicated, STEP 530 is performed in which stimulation is provided in the first mode and a subsequent check is performed in STEP 540.

In alternative embodiments, the check performed in STEP 560 is performed to determine if stimulator 100 should transition to a third mode of stimulation, different than the first or second mode of stimulation. In subsequent steps, not shown, a check can be performed (e.g. via algorithm 106), to determine if the stimulation should transition to either the first mode of stimulation or the second mode of stimulation. In some embodiments, four or more modes of stimulation can be included.

Diagnostic data can be gathered prior to, during or after implantation of one or more portions of the stimulation system, such as diagnostic data gathered at least two weeks after implantation of a stimulator portion. During or after implantation of the implanted stimulator portion, a decision can be made to adjust at least one stimulation parameter based on the diagnostic data. The adjusted parameter can be a stimulation parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; agent delivery rate; physiologic concentration; power of light delivered to tissue; frequency of light delivered to tissue; a modulation parameter of light delivered to tissue; amplitude of sound delivered to tissue; frequency of sound delivered to tissue; a modulation parameter of sound delivered to tissue; mass of agent delivered to tissue; volume of agent delivered to tissue; concentration of agent delivered to tissue; delivery rate of agent delivered to tissue; and combinations of these. Diagnostic data can be used to set initial stimulation parameters and/or to modify existing stimulation parameters.

In some embodiments, repeated stimulation with initial and adjusted stimulation parameters includes incremental increases or decreases of a test stimulation parameter such a series of increases in stimulation voltage and/or current as described hereinabove. In some embodiments, a first stimulation parameter comprises a voltage level below 3.0 Volts, and a second and subsequent test stimulation parameters comprise sequentially increasing the voltage (e.g. in 0.1, 0.2, 0.3, 0.4 or 0.5 Volt increments) until an adverse event and/or a therapeutic benefit is recorded by a diagnostic device of the present inventive concepts. In some embodiments, the stimulation parameter does not exceed a maximum, such as a maximum less than or equal to approximately 10.0 Volts, 9.0 Volts, 8.0 Volts or 7.0 volts. In some embodiments, the voltage or other test stimulation parameter level is increased slowly, such as an increment made in intervals of approximately at least 0.5 seconds, 2.0 seconds, 5.0 seconds, 10.0 seconds or 30.0 seconds.

In some embodiments, a set of stimulation parameters used in multiple steps include at least one test stimulation parameter in which no stimulation is performed (e.g. a test stimulation parameter of 0.0 Volts). In these embodiments, a therapeutic benefit of stimulation can be confirmed (e.g. by the absence of the benefit when no stimulation was given, such as when the diagnostic device comprises a memory test tool as described herein wherein a higher score is achieved with one set of test stimulation parameters).

Figure 3:
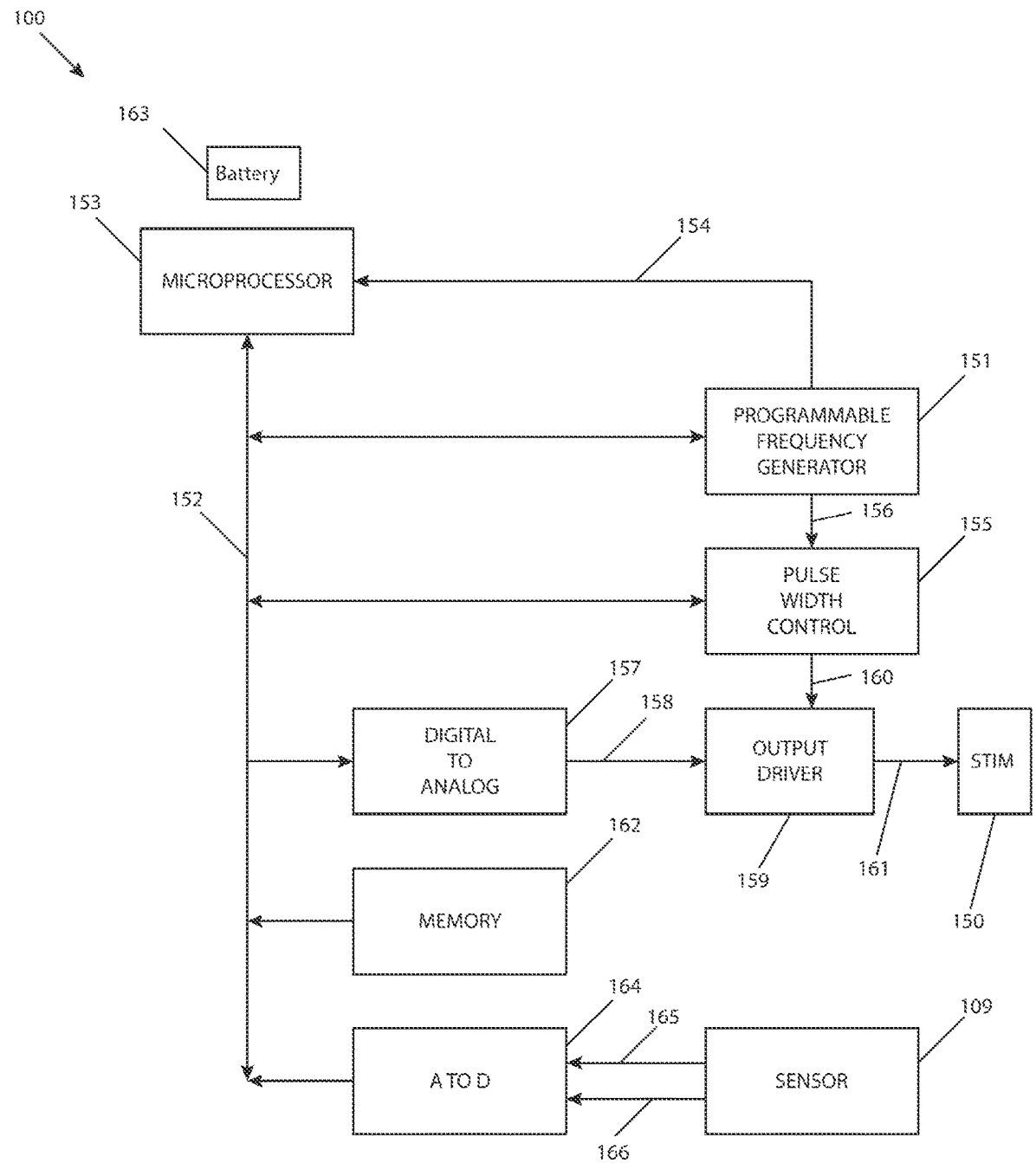
FIG. 3 illustrates a schematic of an electrical brain stimulator, consistent with the present inventive concepts.

Referring now to FIG. 3, a schematic of an electrical stimulation device is illustrated, consistent with the present inventive concepts. Stimulator 100 delivers electrical stimulation energy including a stimulus pulse frequency that is controlled by programming a value to a frequency generator 151 (e.g. a programmable frequency generator) using bus 152. The frequency generator 151 provides an interrupt signal to microprocessor 153 through an interrupt line 154 when each stimulus pulse is to be generated. The programmable frequency generator 151 communicates with a pulse width control module 155 via pathway 156. The frequency generator 151 can be implemented by a commercial device model CDP1878 sold by Harris Corporation. The amplitude for each stimulus pulse is programmed to a digital to analog converter 157 using bus 152. The analog output is conveyed through a conductor 158 to an output driver circuit 159 to control stimulus amplitude.

Microprocessor 153 also programs pulse width control module 155 using bus 152. The pulse width control module 155 provides an enabling pulse of duration equal to the pulse width via a conductor 160. Pulses with the selected characteristics are then delivered from stimulator 100 through cable 161 to stimulation element 150. Stimulation element 150, typically comprising one or more electrodes as are described hereinabove, can be positioned to stimulate the fornix and/or other regions of the brain or other body tissue, also as described hereinabove. At the time that stimulator 100 is implanted, an operator of stimulator 100, such as a clinician, can program certain key parameters into the memory 162 of the implanted stimulator 100, such as via telemetry from an external controller, such as one or more controllers 200 described in reference to FIG. 1 hereinabove. These parameters can be updated subsequently as needed, such as to modify one or more test or treatment stimulation parameters based on diagnostic data produced by a diagnostic device (e.g. diagnostic data 305 produced by diagnostic tool 300 of FIG. 1). Power supply 163 (e.g. one or more batteries) can provide electrical power to one or more components of stimulator 100 described herein.

Stimulation element 150 can comprise one or more deep brain stimulation electrodes, such as electrodes model 3387 produced by Medtronic of Minneapolis, Minn. These electrodes can be bilaterally implanted such that the tips of the electrodes are positioned in a region where cells can be recorded during micro-recording mapping. Alternatively, a single electrode can be implanted unilaterally. Energy can be applied at a frequency of 2 to 1000 Hz, such as at a frequency of approximately 130 Hz. Energy can be delivered at a pulse amplitude, such as at a pulse amplitude of approximately 500 µA. Energy can be delivered at a voltage between 0.1 and 10 Volts, such as at a voltage between 1 Volt and 6 Volts, such as at a voltage of approximately 3 Volts or approximately 3.5 Volts. Energy delivery can be given in a series of on and off times, such as with an on-time of approximately 30 µseconds to 200 µseconds, such as with an on time of approximately 90 µseconds. The duration of energy delivery can range from 30 minutes to 120 minutes, such as a duration of 60 minutes, which can be repeated at regular or irregular intervals. The stimulator can be configured to operate in two or more modes of stimulation, as described in detail hereinabove.

The embodiments of the present inventive concepts can be configured as open-loop systems. A microcomputer algorithm programmed by the clinician sets the stimulation parameters (e.g. stimulation parameters 105a and/or 105b of FIG. 1) of the stimulator 100. This algorithm can change the parameter values over time but does so independent of any changes in symptoms the patient can be experiencing. Alternatively, a closed-loop system discussed below which incorporates a sensor 109 to provide feedback can be used to provide enhanced results. Sensor 109 (e.g. an implanted or external sensor) can be used with a closed loop feedback system in order to automatically determine the level of electrical stimulation necessary to achieve the desired level of improved cognitive function. In a closed-loop embodiment, microprocessor 153 executes an algorithm (e.g. algorithm 106 of FIG. 1) in order to provide stimulation with closed loop feedback control. Such an algorithm can analyze a sensed signal and deliver stimulation therapy (e.g. delivery or electrical, magnetic, light, sound and/or chemical treatment therapy) based on the sensed signal. Adjustments can be made when the signal falls within or outside predetermined values or windows, for example, predetermined levels of BDNF and other neurotrophins (e.g., NGF, CNTF, FGF, EGF, NT-3) and corticosteroids. Closed loop applications can be driven by diagnostic data, such as diagnostic data 305 produced by diagnostic tool 300 described in reference to FIG. 1 hereinabove.

For example, in some embodiments, the patient can engage in a specified cognitive task, wherein the system measures one or more characteristics to determine if the sensed levels are at expected thresholds. If one or more of the sensed characteristics are outside a predetermined threshold, the system can initiate and/or modify the treatment therapy, such as to enhance or otherwise improve cognitive function.

In some embodiments, the system can operate with continuous closed-loop feedback control. In another embodiment, the system can operate in closed-loop feedback control based on a time of day (e.g., during hours that the patient is awake) or based on a cognitive task (e.g., when the patient is working). In yet another embodiment, the system can be switchable between open-loop and closed-loop control by operator control, automatically and/or manually (e.g. manually via a handheld controller).

In some embodiments, the stimulation can be applied before, after and/or during the performance of a memory, cognitive or motor task learning task to facilitate the acquisition of learning or consolidation of the task and in so doing, accelerate the rate of memory acquisition and learning and enhance its magnitude. For example, the stimulation can be provided before, during and/or after periods when the patient is learning a new language or playing a new instrument. Such applied therapy can be useful during the encoding, consolidation and/or retrieval phases of memory. The neuromodulation intervention, brain stimulation via electrical, magnetic, light, sound and/or drug or other agent delivery can occur before, after and/or simultaneous with the memory, cognitive of motor skill task.

In another embodiment, therapy can be provided in relation to learning a task. For example, the stimulation or drug delivery can be applied before, after and/or during the performance of a memory, cognitive or motor task to facilitate the acquisition of learning or consolidation of the task. In so doing, the rate of memory acquisition and learning can be accelerated and enhanced in magnitude. For example, the stimulation or drug delivery can be provided before, during, or after periods when the patient is learning a new language or playing a new instrument. Such therapy can be useful during the encoding, consolidation and/or retrieval phases of memory. The neuromodulation intervention, brain stimulation or drug delivery can occur before, after or simultaneously to the memory, cognitive of motor skill task.

In another aspect of the invention, treatment therapy can be utilized to enhance neurogenesis as a method of improving cognitive function. Techniques for enhancing neurogenesis through treatment therapy are disclosed in co-pending Patent Applications "Cognitive Function Within A Human Brain", U.S. Ser. No. 11/303,293; "Inducing Neurogenesis Within A Human Brain", U.S. Ser. No. 11/303,292; "Regulation of Neurotrophins", U.S. Ser. No. 11/303,619; "Method Of Treating Cognitive Disorders Using Neuromodulation", U.S. Ser. No. 11/364,977; the content of which are each incorporated herein by reference in their entirety.

Referring back to FIG. 3, the system can optionally utilize closed-loop feedback control having an analog to digital converter 164 coupled to sensor 109 via pathways 165 and 166. Output of an A-to-D converter 164 is connected to microprocessor 153 through peripheral bus 152 including address, data and control lines. Microprocessor 153 can process sensor 109 data in different ways (e.g. depending on the type of stimulator in use) and can regulate delivery, via a control algorithm, of stimulation based on the sensed signal. For example, when the signal on sensor 109 exceeds a level programmed by the clinician and stored in a memory 162, increasing amounts of stimulation (e.g. stimulation energy) can be applied through output driver circuit 159. In the case of electrical stimulation, a parameter of the stimulation can be adjusted such as amplitude, pulse width and/or frequency.

Parameters which can be sensed include the activity of single neurons as detected with microelectrode recording techniques, local field potentials, and event related potentials, for example in response to a memory task or sensory stimulus and electroencephalogram or electrocorticogram. For example, U.S. Pat. No. 6,227,203, the content of which is incorporated herein by reference in its entirety, provides examples of various types of sensors that can be used to detect a symptom or a condition of a cognitive disorder and responsively generate a neurological signal. In an embodiment, a neurochemical characteristic of the cognitive function can be sensed, additionally or alternatively. For example, sensing of local levels of neurotransmitters (glutamate, GABA, Aspartate), local pH or ion concentration, lactate levels, local cerebral blood flow, glucose utilization or oxygen extraction can also be used as the input component of a closed loop system. These measures can be taken at rest or in response to a specific memory or cognitive task or in response to a specific sensory or motor stimulus. In another embodiment, an electro-physiological characteristic of the cognitive function can be sensed. The information contained within the neuronal firing spike train, including spike amplitude, frequency of action potentials, signal to noise ratio, the spatial and temporal features and the pattern of neuronal firing, oscillation behavior and inter-neuronal correlated activity can be used to deliver therapies on a contingency basis in a closed loop system. Moreover, treatment therapy delivered can be immediate or delayed, diurnal, constant or intermittent depending on contingencies as defined by the closed loop system.

The foregoing description and accompanying drawings set forth a number of examples of representative embodiments at the present time. Various modifications, additions and alternative designs will become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

What is claimed is:

1. A system for treating a patient, comprising:
   a stimulator for stimulating brain tissue, said stimulator comprising a single lead having a first stimulation element and a second stimulation element; and
   a controller for setting stimulation parameters of the stimulator;
   wherein the stimulator is configured to operate in a first mode with a first set of stimulation parameters and a second mode with a second set of stimulation parameters different than the first set of stimulation parameters;
   wherein the first stimulation element is configured to deliver energy from the stimulator in the first mode and the second stimulation element is configured to deliver energy from the stimulator in the second mode, and wherein the first stimulation element does not deliver energy in the second mode;
   wherein the stimulator is configured to transition between the first mode and the second mode based on a patient awakeness parameter, and wherein the stimulator is configured to transition from the first mode to the second mode when the patient is asleep; and
   wherein the system is configured to treat at least one of a cognitive disease or a cognitive disorder.

2. The system according to claim 1, wherein the system is configured to treat Alzheimer's Disease.

3. The system according to claim 1, wherein the system is configured to provide an enhanced memory recall effect when the stimulator is in the second mode.

4. The system according to claim 1, wherein the stimulator is configured to deliver less energy to brain tissue when in the second mode than the energy delivered to brain tissue when in the first mode.

5. The system according to claim 1, wherein the stimulator is configured to deliver more energy to brain tissue when in the second mode than the energy delivered to brain tissue when in the first mode.

6. The system according to claim 1, further comprising a sensor configured to produce a signal related to patient awakeness, and an algorithm configured to assess patient awakeness based on the sensor signal.

7. The system according to claim 6, wherein the sensor comprises a sensor selected from the group consisting of: electrode; neuronal activity sensor; EEG sensor; polysomnography (PSG) sensor; sleep sensor; sleep state sensor; local field potential sensor; and combinations thereof.

8. The system according to claim 1, wherein the stimulator is configured to stimulate with the first stimulation parameters for multiple discrete first time periods and to stimulate with the second stimulation parameters for multiple discrete second time periods.

9. The system according to claim 1, wherein the cognitive disease or disorder comprises a disease or disorder selected from the group consisting of: Mild Alzheimer's Disease (AD), Moderate Alzheimer's Disease; probable Alzheimer's Disease; a genetic form of Alzheimer's Disease; Mild Cognitive Impairment (MCI); hippocampal damage; hippocampal atrophy due to Alzheimer's disease, anoxia, epilepsy, depression; post-traumatic stress disorder (PTSD); traumatic brain injury (TBI); neuronal loss; neuronal damage; chemotherapy induced memory impairment; epilepsy; a seizure disorder; dementia; amnesia; a memory disorder; a spatial memory disorder; traumatic brain injury; cognitive impairment associated with Schizophrenia; Parkinson's Disease related cognitive impairment or dementia; a neurological condition; a psychiatric condition; and combinations thereof.

10. The system according to claim 1, wherein the magnitude of energy delivered in the first mode is different than the magnitude of energy delivered in the second mode.

11. The system according to claim 10, wherein a difference in the magnitude of energy delivered comprises a difference in energy delivered over time.

12. The system according to claim 10, wherein a difference in the magnitude of energy delivered comprises a difference of at least 10% in magnitude of energy delivered.

13. The system according to claim 1, wherein the stimulation parameter difference comprises a difference in an energy delivery parameter selected from the group consisting of: voltage level; average voltage level, rms voltage level; peak voltage level; current level; average current level, rms current level; peak current level; power level; average power level; rms power level; peak power level; frequency of a stimulation signal; series of frequencies of a stimulation signal; phase of a stimulation signal; pulse width modulation ratio; signal pulse width; current density; current density applied to tissue; single electrode selected to receive stimulation energy; set of electrodes selected to receive monopolar stimulation energy; bipolar stimulation energy; and combinations thereof.

14. The system according to claim 1, wherein the stimulation energy comprises electrical energy, and wherein the stimulation difference comprises a difference in an electrical energy delivery parameter selected from the group consisting of: voltage level; average voltage level; peak voltage level; current level; average current level; peak current level;

power level; average power level; peak power level; frequency; phase; duty cycle; pulse width; modulation; and combinations thereof.

15. The system according to claim 1, wherein the stimulation energy delivered in the first mode comprises energy selected from the group consisting of: electrical energy; magnetic field energy; light energy; energy configured to optogenetically induce neurons; sound energy; chemical energy; and combinations thereof.

16. The system according to claim 1, wherein the tissue stimulated in the first mode comprises a first volume of brain tissue, wherein the tissue stimulated in the second mode comprises a second volume of brain tissue, and wherein at least a portion of the second volume of tissue comprises tissue not included in the first volume of tissue.

17. The system according to claim 16, wherein the second volume of tissue comprises a larger volume than the first volume of tissue.

18. The system according to claim 16, wherein the second volume of tissue comprises the first volume of tissue and tissue not included in the first volume of tissue.

19. The system according to claim 1, wherein the stimulator is further configured to operate in a third mode with a third set of stimulation parameters different than the first set of stimulation parameters and the second set of stimulation parameters.

20. The system according to claim 1, further comprising a diagnostic tool for measuring at least one patient parameter and producing diagnostic data representing the at least one measured patient parameter; and
wherein the stimulator transitions between the first mode and the second mode based on the diagnostic data.

21. The system according to claim 1, wherein the brain tissue stimulated comprises at least a portion of the fornix.

22. The system according to claim 21, wherein the brain tissue stimulated further comprises non-fornix brain tissue.

23. The system according to claim 1, wherein the brain tissue stimulated comprises brain tissue selected from the group consisting of: fornix; entorhinal cortex; hippocampus; anterior thalamic nucleus; amygdala; mammillary bodies; parahippocampal cortex; temporal neocortex; septal nuclei; nucleus basalis of Meynert; subcallosal or subgenual cingulate; ventral capsule; ventral striatum and combinations thereof.

24. The system according to claim 1, wherein the brain tissue stimulated does not comprise tissue selected from the group consisting of: hippocampal tissue; optical tract tissue; and combinations thereof.

25. The system according to claim 1, further comprising an awakeness sensor, wherein the controller is configured to assess the patient's sleep state based on a signal provided by the awakeness sensor.

26. The system according to claim 25, wherein the awakeness sensor comprises an EEG sensor.

* * * * *